United States Patent [19]

Reddy et al.

[11] Patent Number: 5,869,696
[45] Date of Patent: Feb. 9, 1999

[54] UNIVERSAL SOLID SUPPORTS AND METHODS FOR THEIR USE

[75] Inventors: M. Parameswara Reddy, Brea; Maged A. Michael, Placentia; Firdous Farooqui, Brea, all of Calif.

[73] Assignee: Beckman Instruments, Inc., Fullerton, Calif.

[21] Appl. No.: 636,113

[22] Filed: Apr. 22, 1996

[51] Int. Cl.$^6$ .................. C07C 211/04; C07C 211/05; C07C 295/027; C07C 295/03
[52] U.S. Cl. .................. 548/564; 536/25.3; 536/25.34; 536/25.4; 546/184; 564/463; 564/499
[58] Field of Search ................ 564/463, 499; 548/564; 546/184

[56] References Cited

U.S. PATENT DOCUMENTS

| | | | |
|---|---|---|---|
| 2,068,132 | 1/1937 | Herold et al. | 564/499 |
| 2,547,064 | 4/1951 | Tyerman | 564/499 |
| 2,657,237 | 10/1953 | Isham | 564/499 |
| 3,271,455 | 9/1966 | Cook et al. | 564/499 |
| 4,552,957 | 11/1985 | McEntire | 564/499 |
| 5,189,221 | 2/1993 | Duranleau et al. | 564/499 |

OTHER PUBLICATIONS

"A Universal Glass Support For Oligonucleotide Synthesis," J.S. de Bear, *Nucleosides & Nucleotides*, 6(5), 821–830 (1987).

"A Universal Adapter for Chemical Synthesis of DNA or RNA on any Single Type of Solid Support," M.E. Schwartz, *Tetrahedron Letters*, vol. 36, No. 1, pp. 27–30 (1995).

Tetrahedron Report Number 309, "Advances in the Synthesis of Oligonucleotides by the Phosphoramidite Approach," S. Beaucage, *Tetrahedron*, vol. 48, No. 12, pp. 2223–2311 (1992).

"Synthesis of oligonucleotides on cellulose by a phosphotriester method," R. Crea, *Nucleic Acids Research*, vol. 8, No. 10 (1980).

Yu, C.J., "A universal support and modified ammonia deprotection for synthesis of oligonucleotides: DNA oligomer synthesis," by BioGenex, San Ramon, CA, AACC Nucleic Acid Conference in San Diego, CA, Abstract No. 51 (1995).

*Primary Examiner*—Richard L. Raymond
*Attorney, Agent, or Firm*—William H. May; P. R. Harder; Fulbright & Jaworski

[57] ABSTRACT

Universal solid support oligonucleotide synthesis reagents, oligonucleotide synthesis processes, and reagents for cleaving oligonucleotides from solid supports are disclosed. Oligonucleotide synthesis reagents have the following general formula:

$$SS-R^6-O-R^3 \qquad \text{I}$$

wherein SS is a solid support; $R^6$ is

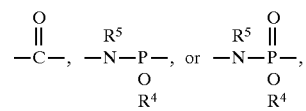

where $R^5$ is hydrogen or alkyl and $R^4$ is a phosphate protecting group; and $R^3$ is a ring moiety having vicinal groups $-XR^1$ and $-YR^2$ wherein each of X and Y is independently selected from the group consisting of O, S and NH and one of $R^1$ and $R^2$ is a blocking moiety and the other is hydrogen or a hydroxy protecting group. Oligonucleotide cleaving reagents include methylamine and/or ammonium hydroxide and trimethylamine.

10 Claims, No Drawings

UNIVERSAL SOLID SUPPORTS AND METHODS FOR THEIR USE

BACKGROUND OF THE INVENTION

The present invention relates generally to the fields of chemistry and biology. More particularly, the present invention is directed to compositions and methods for use in the synthesis of oligonucleotides (e.g., DNA and RNA sequences).

A variety of synthetic approaches have been developed for preparation of oligonucleotide sequences. Typically, oligonucleotides are synthesized utilizing a building block approach which involves the sequential addition of nucleotides onto a growing oligonucleotide chain immobilized on to a solid support. Because every DNA oligonucleotide may have any of 4 different initial nucleotides, it is necessary to maintain a supply of 4 different nucleoside (A, C, G and T) loaded solid supports to be able to synthesize any given DNA sequence. In the case of DNA synthesis, the first nucleoside from the 3' end of the DNA sequence is typically preloaded on the solid support through an ester linkage. For example, if the sequence that is to be synthesized contains a T nucleoside at the 3' end, a T support is employed and the balance of the nucleotides in the DNA sequence added thereto (for example, using an automated DNA synthesizer). At the end of the total DNA synthesis, the oligonucleotide is cleaved from the solid support through the hydrolysis of the ester linkage. Taking into consideration RNA synthesis procedures, an additional 4-different nucleoside loaded solid supports must be available to the user. Similar considerations apply if any specialty modified nucleoside is desired at the 3' end.

Maintaining a supply of at least 8 different prederivatized solid supports is inconvenient and expensive. An additional consideration is the relatively short shelf life of nucleoside derivatized solid supports. Typically, after one year storage such solid supports are not longer usable. There is also the possibility that synthetic procedures may be initiated mistakenly with the wrong support leading to disastrous consequences in the final applications of the oligonucleotides.

In order to alleviate these problems some researchers have pursued developing some type of universal solid support. For example, deBear et al. derivatized glass supports with 2' (3')-O-benzoyluridine 5'-O-succinyl so that the uridine moiety is linked to the glass via an ester (succinate) linkage. [de Bear et al., Nucleosides and Nucleotides 6, 821–830 (1987)]. Oligonucleotide synthesis takes place by adding nucleotide monomers to the 2' or 3' position of the uridine. Following the synthesis, the new oligonucleotides can be released from the glass, deprotected and cleaved from the uridylyl terminus in one reaction. Since the uridyl functionality is cleaved from the solid support in this cleaving reaction, the support is not available for subsequent oligonucleotide syntheses.

Crea and Horn suggested a similar approach which involved preparing the dimer 5'-O-p-chlorophenylphospho-2' (3')-O-acetyluridilyl-[2' (3')-3']-5'-O-dimethoxytritylthymidine p-chlorophenylester and attaching the dimer to cellulose via a phosphate linkage. The 5' position of the thymidine is available for oligonucleotide attachment and synthesis. [R. Crea & T. Horn, Nucleic Acids Research 8, 2331 (1980)]. The subsequent use of aqueous concentrated ammonia results in the release of the synthesized oligonucleotide from the cellulose leaving the uridine portion of the dimer attached to the cellulose. Although Crea and Horn utilized the reactive vicinal groups on the uridine as the release site for the oligonucleotide from the uridine the solid support suggested in this reference is not a universal solid support since the initial oligonucleotide is incorporated in the solid support reagent and a different support is required for oligonucleotides incorporating different first nucleoside.

More recently, Schwartz et al. attached an adapter, 2' (3')-O-dimethoxytrityl-3' (2')-O-benzoyluridine-5'-O-(2-cyanoethyl N,N-diisopropylphosphoramidite, to a thymidine derivatized polystyrene and synthesized an oligonucleotide from the O-dimethoxytrityl position of the uridine. [M. E. Schwartz, R. R. Breaker, G. T. Asteriadis, and G. R. Gough, Tetrahedron Letters, Vol. 36, No. 1, pp 27–30, 1995] While this approach provides a universal solid support for oligonucleotide synthesis, the cleaving step releases the adapter and the thymidine from the support and then cleaves the synthesized oligonucleotide from the uridine. Thus, the purification process requires removing the thymidine linker and the cleaving processes leaves the solid support unavailable for subsequent uses.

The aforementioned solid supports and methods for their use disadvantages in terms of the convenience and efficiency of the subsequent oligonucleotide cleaving steps. When ammonia which has been widely accepted as a safe reagent for DNA synthesis is utilized for cleaving, as taught by deBear et al., the cleavage time is as long as 24 hours at 65° C. In view of the growing trend to produce oligonucleotides as quickly as possible, this is an unacceptably long period of time. Decreasing the time required for cleaving the uridylyl from an oligonucleotide at the uridine 3' position typically uses a lead (II) ion catalyst system or the action of strong alkali hydroxides. Necessarily these processes require a separate isolation step to remove the lead ion. Additionally, when strong alkali bases are used in the cleaving processes, considerable side reactions in the form of cytosine deamination occur.

Recent improvements in the automation of simultaneous multiple oligonucleotide synthesis (whereby several oligonucleotides are synthesized simultaneously) further highlight the desirabilty of using a single universal solid support for the synthesis of oligonucleotides. Any requirement to dispense several different nucleoside preloaded solid supports on a DNA synthesizer clearly complicates the synthesis automation. Therefore, it would be highly desirable to have a universal solid support to synthesize any nucleic acid.

It is an object of the present invention to provide methods and compositions for use in the synthesis of oligonucleotides which ameliorate some of the problems encountered with the prior art methods and compositions. More particularly, it is an objective of the present invention to provide reusable oligonucleotide synthesis reagents which can be used for synthesizing a variety of oligonucleotide independent of the initial nucleoside. It is another objective to provide cleaving reagents and cleaving methods which substantially decrease the time required to cleave oligonucleotides after synthesis.

SUMMARY OF THE INVENTION

The present invention provides methods and compositions which overcome prior art problems associated with the solid support synthesis of oligonucleotides. The methods and compositions of the present invention provide a single reusable universal solid support suitable for step-wise oligonucleotide synthesis and the subsequent single step cleavage and deprotection of the synthesized oligonucleotide. In another aspect, the present invention provides cleaving reagents suitable for removing oligonucleotides from the solid support to which they are synthesized. The cleaving reagents of the present invention are volatile and thus do not require subsequent time consuming reagent removal processes. Moreover, the cleaving reagents of the present invention remove synthesized oligonucleotides in a substantially reduced length of time.

More particularly, the present invention provides an oligonucleotide synthesis reagent having the following general formula:

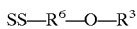

wherein SS is a solid support; $R^6$ is

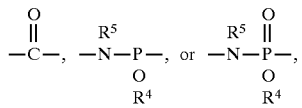

where $R^5$ is hydrogen or alkyl and $R^4$ is a phosphate protecting group; and $R^3$ is a ring moiety having vicinal groups —$XR^1$ and —$YR^2$ wherein each of X and Y is independently selected from the group consisting of O, S and NH and one of $R^1$ and $R^2$ is a blocking moiety and the other is hydrogen or a hydroxy protecting group. Preferably $R^3$ is a sugar moiety with —$XR^1$ and —$YR^2$ occupying the second and third carbon positions of the sugar ring. Most preferably $R^3$ has the structure

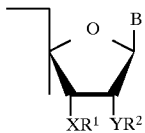

wherein B is a purine or pyrimidine base; each of X and Y and $R^1$ and $R^2$ are as described above. Preferred $R^1$ or $R^2$ blocking moieties are alkylcarbonyl or arylcarbonyl which can be prepared by forming an ester blocking group at one of two vicinal hydroxy functionalities. Preferred embodiments of $R^6$ are the phosphoramidite linkages and the oxidized form, phosphoramidate linkages, characterized when $R^6$ is

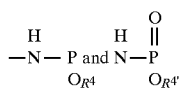

respectively and phosphate protecting group $R^4$ is a cyanoethyl moiety. Advantageously, these reagents are useful as universal solid supports in the synthesis of oligonucleotides where the synthesis takes place at the vicinal $R^1$ or $R^2$ position having the hydroxy protecting group; the other $R^1$ or $R^2$ position being blocked with the arylcarbonyl or alkylcarbonyl blocking moiety. Surprisingly, it has been determined that the post synthesis release of oligonucleotides synthesized using the oligonucleotide synthesis reagents of the present invention is substantially faster than the release of oligonucleotides utilizing prior art solid support reagents. Moreover, the oligonucleotides are released at the vicinal group position of the ring moiety. When the link between the ring moiety and the solid support is a phosphoramidate or phosphoramidite the release does not effect the solid support bond, and oligonucleotide reagent is suitable for repeat synthesis procedures.

In accordance with another aspect of the present invention, there are provided cleaving methods and cleaving reagents for releasing oligonucleotides from a solid support. The cleaving reagents and releasing methods described herein are applicable to oligonucleotides attached to a variety of solid supports including ester linked oligonucleotides, phosphate linked oligonucleotides and phosphoramidate or phosphoramidite linked oligonucleotides. Cleaving methods of the present invention involve contacting a solid support bearing an oligonucleotide with a cleaving reagent of the present invention which comprises a mixture of a first compound which includes methylamine and/or ammonium hydroxide and a second compound which can be a secondary amine and/or a tertiary amine. Preferably, the cleaving reagent is in the range of about 1:9 (v/v) of 40 wt % aqueous methylamine: 23–25 wt % aqueous trimethyl amine to about 9:1 (v/v) 40 wt % aqueous methylamine:23–25 wt % aqueous trimethyl amine.

These and other advantages well become evident to those skilled in the art upon a more thorough understanding of the present invention as described in the following more detailed description of the invention.

DETAILED DESCRIPTION OF THE INVENTION

The present invention provides improvements in compositions and methods for solid support based oligonucleotide synthesis. More particularly, the present invention provides oligonucleotide synthesis reagents in which a ring moiety is linked to a solid support via a phosphoramidate linkage. The ring moiety has vicinally positioned functionalities, one of which is the site for the step wise synthesis of oligonucleotides and the other of which is blocked during the synthesis but is unblocked to become active during the cleaving process. The oligonucleotide synthesis reagent of the present invention is a universal solid support in that a single oligonucleotide reagent is useful for the synthesis of any oligonucleotide having any initial nucleoside, thus precluding the need to maintain a variety of different suitably derivatized solid supports. Moreover, because during typical cleaving processes the phosphoramidate bond of the present oligonucleotide reagent remains stable, synthesis reagents of the present invention can be used for subsequent oligonucleotide syntheses.

In such systems, two hydroxyls (or equivalents thereto, as hereinafter defined) are linked to adjacent carbon atoms, preferably in a cis-orientation. For oligonucleotide synthesis, one of the two hydroxyls or hydroxyl equivalents is blocked; preferably, hydroxyl is blocked in the form of an ester derivative of the hydroxyl or hydroxyl equivalent. Compositions in which either one of the hydroxyls or equivalent or a mixture of both hydroxyls or equivalents may suitably be employed. The remaining unblocked vicinal site is used to grow the oligonucleotide chain. Typically, this site is protected with a suitable protecting group, for example DMT, (dimethoxytrityl), and then deprotected just prior to adding the initial nucleotide in the synthesis.

At the end of the synthesis, the blocked vicinal site is unblocked or hydrolysed to liberate the hydroxyl or equivalent. The hydroxyl or equivalent then makes an intramolecular attack on the adjacent phosphate group of the first nucleotide of the oligonucleotide chain, forming a cyclic phosphate. This results in the release of the oligonucleotide molecule from the solid support. Whatever nucleoside is first added to the solid support during the oligonucleotide synthesis becomes the 3'-end terminal nucleoside of the synthesized molecule (when the oligonucleotide is synthesized in the conventional 3' to 5' direction).

In accordance with a first aspect of the present invention, there are provided oligonucleotide synthesis reagents having the general formula I

SS—R⁶—O—R³    I wherein SS is a solid support; R⁶ is

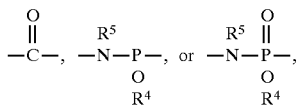

where R⁵ is hydrogen or alkyl and R⁴ is a phosphate protecting group; and R³ is a ring moiety having vicinal groups —XR¹ and —YR² wherein each of X and Y is independently selected from the group consisting of O, S and NH and one of R¹ and R² is a blocking moiety and the other is hydrogen or a hydroxy protecting group suitable for protecting —OH, —SH, or —NH₂. Recognizing that when R⁶ is a phosphoramidite or its oxidized form, phosphoramidate, those skilled in the art will appreciate that R⁵ is preferably hydrogen. This is because these oligonucleotide synthesis reagents are generally prepared using a primary amine. However, those skilled in the art will also appreciate that R⁵ can be alkyl because the phosphoramidate can be prepared using secondary amines.

Phosphate protecting group R⁴ is suitably any group capable of protecting the phosphorous of the phosphoramidate or phosphoramidite from cleaving or reacting during oligonucleotide synthesis. Those skilled in the art will recognize that cyanoethyl moieties are preferred phosphate protecting groups for their stability under oligonucleotide synthesis conditions and their ease of removal with ammonia or methylamine. However, it will be understood that because the phosphoramidate or phosphoramidite linkage of the utilized in the present invention need not be deprotected and thus alkyl moieties generally or aryl containing moieties are also suitable phosphate protecting groups R⁴.

For reasons described below, vicinal groups —XR¹ and —YR² are most effective when they are positioned cis with respect to each other. Since adjacent functionalities attached to ring moieties can be present in a cis configuration, R³ is preferably a ring moiety and —XR¹ and —YR² are oriented in space in a fixed cis position. However, R³ can be straight chained moieties having suitable vicinal constituents, such as glycerol. Because many sugars are ring systems having vicinally positioned hydroxy functionalities, R³ is preferably a sugar with —XR¹ and —YR² occupying the second and third carbon positions of the sugar ring. For reasons described below, nucleosides, or sugars having an attached purine or pyrimidine base are particularly preferred ring moieties. Most preferably R³ has the structure:

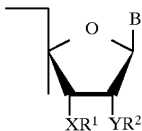

wherein B is a purine or pyrimidine base; each of X and Y is independently selected from the group consisting of O, S and NH; one of R¹ and R² is an alkylcarbonyl or arylcarbonyl group and the other of R¹ and R² is hydrogen or a protecting group suitable for protecting —O, —S, or —NH. Because of its availability and ease of use B is preferably uridine.

Those skilled in the art will appreciate that because of their availability on sugars and glycerol type diols, and because of known protecting groups suitable for their protection, X and Y are preferably O (oxygen). However, it will be apparent to those skilled in the art that utilizing NH and S in such positions for the purposes of the present invention is within the scope of the present invention.

In order to block one of the vicinal positions from participating in the oligonucleotide synthesis R¹ or R² is a suitable blocking group,. Because, as described below, the unblocked X or Y is active in the final oligonucleotide cleaving step, the blocking group must be easily removed under cleaving reaction conditions but stable under those conditions typically found in oligonucleotide synthesis. For this reason one of R¹ or R² is preferably an alkylcarbonyl or arylcarbonyl. An alkylcarbonyl moiety is an aliphatic group terminating in C=O, wherein the aliphatic component comprises one (i.e., Acetyl) to about 10 carbon atoms. By an arylcarbonyl group is meant a residue comprising at least one homoaromatic or heteroaromatic ring and terminating in C=O (e.g., $C_6H_5CO$).

The hydroxyl—protecting group associated with the R¹ or R² which is not a blocking group is suitably any protecting group which is easily removed so that the protected group is available as the site for the introduction of a first nucleoside during the initiation of oligonucleotide synthesis. For purposes of the present invention, the 4,4'-dimethoxytrityl (DMT) group is particularly preferred. Other suitable groups include, but are not limited to, the following: 4,4',4"-tris-(benzyloxy)trityl (TBTr); 4,4',4"-tris-(4,5-dichlorophthalimido)trityl (CPTr); 4,4',4"-tris(levulinyloxy)trityl (TLTr); 3-(imidazolylmethyl)-4,4'-dimethoxytrityl (IDTr); pixyl (9-phenylxanthen-9-yl); 9-(p-methoxyphenyl)xanthen-9-yl (Mox); 4-decyloxytrityl ($C_{10}Tr$); 4-hexadecyloxytrityl ($C_{16}Tr$); 9-(4-octadecyloxyphenyl)xanthene-9-yl ($C_{18}Px$); 1,1-bis-(4-methoxyphenyl)-1'-pyrenyl methyl (BMPM); p-phenylazophenyloxycarbonyl (PAPoc); 9-fluorenylmethoxycarbonyl (Fmoc); 2,4-dinitrophenylethoxycarbonyl (DNPEoc);4-(methylthiomethoxy)butyryl (MTMB); 2-(methylthiomethoxymethyl)-benzoyl (MTMT); 2-(isopropylthiomethoxymethyl)benzoyl (PTMT); 2-(2,4-dinitrobenzenesulphenyloxymethyl)benzoyl (DNBSB); and levulinyl groups. These and other suitable protecting groups are described in detail in Beaucage, S. L. and Iyer, R. P. Tetrahedron 48, 2223–2311 (1992), the entire disclosure of which is hereby incorporated by reference.

For purposes of the present invention, B represents a pyrimidine or purine base. Preferred for use in accordance with the present invention are those bases characteristic of guanine, adenine, thymine and cytosine; however, other purine or pyrimidine bases as may be employed in the synthesis of nucleotide analogs may alternatively be used as group B.

As will be evident from the examples described herein preferred oligonucleotide synthesis reagents of the present invention have the following structures:

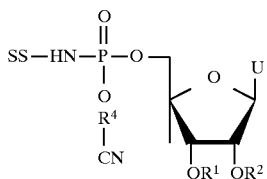

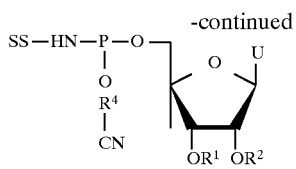

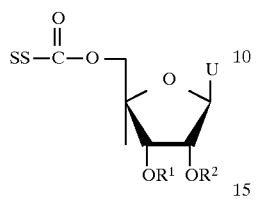

As would be readily appreciated by those working in the field, a wide variety of solid supports as are conventional for use in oligonucleotide synthesis may be employed. The solid support comprises a functional group for attachment of a suitable phosphoramidite to form a phosphoramidate linkage, substituted phosphoramidite linkage or suitable ester linkage thereto by routine methods; common functional groups include hydroxyl, sulfhydryl and amino. The following exemplary supports have been employed: CPG [Pon, R. T. et al., Biotechniques 6, 768 (1988); Adams, S. P. et al., J. Amer. Chem. Soc. 105, 661 (1983)]; Fractogel [sold by E. Merck, Darmstadt, Germany, under the name "Fractogel" and by TosoHaas, Philadelphia, Pennsylvania, under the name "Toyopearl"; Reddy, M. P. et al., Tetrahedron Letters 35, 5771–5774 (1994)]; and tentagel [available from Rapp Polymere, Tubingen, Germany; Andrus et al., Tetrahedron Letters 34, 3373–3376 (1993)]. It will be understood by those skilled in the art that the solid support can be derivatized with a spacer linkage having a suitable functional group for forming the linkage to the vicinal reactive groups. Such spacer linkages are favored by some because the can act as a leash in distancing the solid support.

Other supports conventionally used in DNA synthesis [for example, as described in, e.g., Gait, M. J., Oligonucleotide Synthesis: A Practical Approach, IRL Press (1984) and U.S. Pat. No. 4,923,901] would also be suitable for use in accordance with the present invention. Solid supports are suitably useful in a resinous or particulate form, other preformed shapes of any size, fibers, films etc.

Advantageously, the oligonucleotide synthesis reagent of the present invention can be used in any oligonucleotide synthesis method capable of utilizing an unprotected or protect —OH, —SH, —$NH_2$ include those methods using phosphoramidite reagents, the most widely used coupling chemistry for synthesis of oligonucleotides. However, other coupling chemistries are equally suitable for use, such as H-phosphonate chemistry [U.S. Pat. No. 4,959,463; Froehler, B. C. et al., Nucleic Acids Research 14, 5399 (1986)] and triester chemistry [Stec, W. J. et al, Tetrahedron Letters 26, 2191 (1985); Gallo, K. O. et al, Nucleic Acids Research 14, 7406 (1986); Gait, M. J., Oligonucleotide Synthesis: A Practical Approach, IRL Press (1984)]. Thus, various kinds of nucleic acids may be employed in synthesis of oligonucleotides. The products which may be synthesized include DNA, RNA, oligonucleoside methylphosphonates [Agarwal, S. & Goodchild, J., Tetrahedron Letters 28, 3539 (1987)], oligonucleoside phosphorothioates [Beaucage, S. L. et al., J. Am. Chem. Soc. 112, 1253 (1990)], oligonucleoside phosphorodithioates [Dahl, O. & Bjergade, K., Nucleic Acids Research 19, 5843 (1991)], circular oligonucleotides [Kool, E. T. & Wang, S., Nucleic Acids Research 22, 2326 (1994); Kool, E. T. et al., J. Amer. Chem. Soc. 115, 360 (1993)], 2'-OMe RNA [Sproat, B. S. et al., Nucleic Acids Research 18, 41 (1989)], and products containing peptide nucleic acids [Nielsen, P. E. et al., Bioconjugate Chem. 5, 3 (1994)] or morpholine type backbone modified nucleic acids [Stirchak et al., Nucleic Acids Research 17 6129 (1989); U.S. Pat. No. 5,034,506].

Synthesis on a solid support in the manner described herein also provides the option of generating a solid support tethered oligonucleotide. The support tethered oligonucleotide can be used in a variety of applications, such as DNA affinity extractions and reverse blot hybridization. In one approach, at the end of the oligonucleotide synthesis, the solid support is treated at to room temperature with methylamine for about 1 hour to remove protecting groups from the heterocyclic amino groups of purine and pyrimidine bases contained in the nucleosides. This treatment releases only a minor amount of the oligonucleotide from the solid support, leaving the major portion of the oligonucleotide intact on the solid support. This provides biologically active oligonucleotide still attached to the solid support.

In another approach, the adjacent hydroxyl is protected by a group such as silyl. In such systems, the oligonucleotides stay bound to the support after the treatment with, for example, $CH_3NH_2$. However, the silyl group can be removed, for example by tetrabutylammonium fluoride, thus liberating the hydroxyl; under basic conditions, the liberated hydroxyl attacks the adjacent phosphate, thus releasing the DNA from the solid support.

In accordance with another aspect of the present invention, there are provided methods for cleaving an oligonucleotide from a solid support and reagents useful for cleaving oligonucleotides from a solid support to which they have been synthesized. Preferably, the cleaving reagents and cleaving methods of the present invention have application in oligonucleotide synthesis systems wherein the oligonucleotide is synthesized in the step-wise addition of nucleoside from one hydroxyl or equivalent thereof of a vicinal diol pair or functional equivalent thereof. Most preferably, the oligonucleotide reagent has utility in cleaving oligonucleotides synthesized utilizing the oligonucleotide synthesis reagent of the present invention. However, the methods and cleaving reagents of the present invention are equally useful for cleaving oligonucleotides attached to solid supports through ester linkages and phosphate linkages.

In particular the cleaving methods of the present invention involve contacting the solid support bearing an oligonucleotide with a cleaving reagent of the present invention which includes a mixture of a an amine selected from the group consisting of tertiary amines and secondary amines and a base selected from the group consisting of ammonium hydroxide and a primary amine. A most preferred cleaving reagents is a solution of trimethylamine and methylamine. Additional secondary and tertiary amines suitable in the practice of the present invention include a variety of amines (bases with higher pKa's) such as triethylamine, n-propylamine, diisopropylamine, diisopropylethylamine, dimethylamine, diethylamine, piperidine, N-methylpiperidine and N-methylpyrrolidine. Preferred tertiary amines include trimethylamine, triethylamine, N-methylpyrrolidine, and diisopropylethylamine. As is demonstrated below the amount of ammonium hydroxide or primary amine and the amount of secondary amine or tertiary amine in the cleaving reagent can vary considerably. For example, in preferred cleaving reagents a ratio of methylamine or ammonium hydroxide to a secondary amine or tertiary amine is within the range of about 1:100 to about 100:1. Preferred concentration ratios and constituents are at least 9 parts of an aqueous methylamine solution to one part organic base having a basicity greater than ammonia. The most preferred cleaving reagent is 1 part of 40 wt % aqueous methylamine to 1 part of 3–25 wt % trimethylamine. (Those skilled in the art recognize the methylamine and trimethylamine are gases at standard temperature and pressure and their typical availability is in the form of an aqueous solution.

Typically aqueous methylamine is 40 wt % methylamine and typical concentrations of trimethylamine are in the range of 23–25 wt %. As used in the context of the present invention, reference to a 1:1 v/v solution of methylamine and trimethylamine refers to a 1:1 v/v of a 40 wt % methylamine and about 24 wt % solution of trimethylamine.)

It is further contemplated within the scope of the present invention to include inorganic salts in cleaving reaction mixtures in order to enhance the cleaving kinetics. Such salts are typically salts of Li or Na, however, other cations are also suitable, including Mn and Mg. It has been discovered that when 0.5M LiCl is utilized in a cleaving reagent of 1:1 methylamine:trimethylamine the amount of oligonucleotide cleaved after 15 minutes at 65° C. increases from about 45% (in the absence of LiCl) to about 65 minutes.

In accordance with the present invention the rate of cleavage of the oligonucleotide from the solid support is affected by the nature of a bond between the solid support and the oligonucleotide synthesis site. More particularly, cleaving reactions involving oligonucleotides synthesized at vicinal sites bound to a solid support through ester linkages first involve hydrolysis of the ester linkage and the subsequent cleaving of the oligonucleotide from the vicinal site. Relative to the use of an aliphatic ester linkage to attach the binding group comprising a vicinal diol group to the solid support, use of phosphoramidate linkages facilitate faster cleavage kinetics.

In the case of the ester linkage (as described in deBear et al.), the ester is first hydrolyzed in about 5 minutes. This releases the oligonucleotide and linking group containing from the solid support. Detachment of the linking group from the oligonucleotide then requires additional incubation for about 4 hours at 65° C.

In the case of utilizing the oligonucleotide synthesis reagents having a phosphoramidate linkage in accordance with the present invention, the oligonucleotide is released from the vicinal reactive site and the phosphoramidate bond remains intact still attached to the support. This cleaving reaction can be accomplished utilizing a 1:1 v/v methylamine/trimethylamine cleaving reagent, (as described above) in approximately 90 minutes at 65° C. Significant amounts of the oligonucleotide are released from the linkage in a substantially less amount of time. That is, about 60% of the oligonucleotide will release after a reaction time of 15 minutes. This suggests that the phosphoramidate group of the linking group is accelerating the cleavage of the vicinal diol system from the nucleic acid.

In examining the cleavage of oligonucleotide from vicinal diol systems attached to a solid support through an ester link, it was noted that using concentrated ammonia at 65° C. required an incubation time of as long as 24 hours, which is a commercially undesirable length of time. When methylamine/ammonia was used, the cleavage time was reduced to 12 hours; however, the reduction in the time is not as great as anticipated based on the reactivity of methylamine. It has been reported [Reddy, M. P. et al., Tetrahedron Letters 35, 4311 (1994); U.S. Pat. No. 5,348,868] that methylamine is about 10 times more reactive than ammonia in causing the hydrolysis of esters by virtue of its higher nucleophilicity. Since methylamine showed only about a two-fold acceleration of kinetics, it was suspected that methylamine may be acting merely as a stronger base than ammonia, and not as a stronger nucleophile. This suggests that a stronger base might be needed to activate one hydroxyl of the vicinal diol system to make an attack on the adjacent hydroxyl.

Accordingly, a variety of stronger organic bases (bases with higher pKa's) such as trimethylamine, triethylamine, n-propylamine, diisopropylamine, diisopropylethylamine, dimethylamine, diethylamine, piperidine, N-methylpiperidine and N-methylpyrrolidine were employed as a 1:1 mixture with methylamine. Methylamine was used to remove protecting groups from the heterocyclic amino groups of the oligonucleotide and to remove phosphate protecting group of the nucleosides in the oligonucleotide being synthesized. Using these exemplary compositions, the cleavage time has been reduced to anywhere between 3 hours and 7 hours.

The method of the present invention is suitable for cleaving oligonucleotides from virtually any type of vicinal diol or equivalent system used for oligonucleotide synthesis. Such systems may be described by the general formula

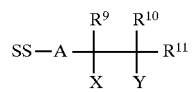

in which S is a solid support, A is a linking group, X and Y are independently selected from the group consisting of —OH, —SH and —NH$_2$, and R$^9$, R$^{10}$ and R$^{11}$ are substituents which do not interfere with the oligonucleotide synthesis reaction. Those skilled in the art will recognize that amino or thiol groups under certain conditions may provide advantages in terms of offering more stability and/or providing faster kinetics of release of nucleic acids from the solid support. In preferred systems, two of R$^9$, R$^{10}$ and R$^{11}$ together comprise a single moiety which (in combination with the carbons bearing the X and Y substituents) form a ring system. For Example, the kinetics of cleavage is faster with a uridine system as compared to a glycerol system, probably due to the free rotation around the glycerol C—C bond, which may be less conducive to the formation of the cyclic phosphate. In the case of the preferred systems (such as those comprising uridine), the hydroxyls are locked in a cis-configuration which is conducive to the formation of the cyclic phosphate. A wide variety of other vicinal diol systems (such as, for example, dihydroxycyclopentane, dihydroxycyclohexane and anhydroerythritol) would also be suitable.

Those skilled in the art will recognize that the blocking moiety at a vicinal position of the oligonucleotide synthesis reagents of the present invention or other relevant solid support systems does not effect the overall cleavage time utilizing the reagents of the present invention. That is, the cleaving time does not have any bearing on whether the group was protected by, e.g., an acetyl group or a benzoyl group. This further confirms that the ester hydrolysis (i.e., removal of the protecting group from the hydroxyl) is a non-rate limiting fast step whereas the attack of the liberated hydroxyl on the adjacent phosphorous of the synthesized oligonucleotide is a rate limiting slower step.

The invention may be better understood with reference to the accompanying examples, which are provided for purposes of illustration only and should not be construed as in any sense limiting the scope of the present invention as defined in the claims appended hereto.

EXAMPLES

Example 1

Synthesis of 2' (3')-O-acetyl-2' (3')-O-(4,4'-dimethoxytrityl)-uridine-5'-O-(N,N-diisopropyl)-β-cyanoethyl-phosphoramidite The following example describes the synthesis of a phosphoramidite reagent suitable for preparing an oligonucleotide synthesis reagent of the present invention.

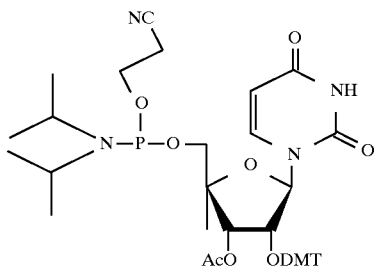

2' (3')-O-Acetyl-2' (3')-O-(4,4'-dimethoxytrityl)-uridine (0.65 g, 1.1 mmole) was dried by successive co-evaporation with pyridine, toluene and THF. The dried residue was dissolved in dry THF (5 ml) and N,N-diisopropylethylamine (0.85 ml, 4 mmole) was added followed by the dropwise addition of β-cyano-ethylmonochloro-N,N-diisopropylphosphoramidite (0.5 ml, 2 mmole) using a syringe with constant stirring under argon at room temperature over 5 minutes. After 60 minutes of additional stirring, the reaction mixture was evaporated to dryness and the residue was dissolved in ethyl acetate (50 ml), washed with 10% $NaHCO_3$ solution (2×50 ml) and dried over $Na_2SD_4$. After removing the ethyl acetate under reduced pressure, the residue was purified using silica gel (pre-heated at 100–120° C.) column-chromatography. The column was packed with the pre-heated silica gel in ethyl acetate/diisopropylamine, 95/5 v/v and eluted with ethyl acetate. The fractions which contained the product were collected, evaporated under reduced pressure and dried using high vacuum to provide the title compound as a white solid (0.6 g, 69% yield).

The $^1$H-NMR in $CDCl_3$ was as follows: δ 1.19 (m,12H, 2 $CH(CH_3)_2$), 1.97 (d, 3H, $COCH_3$), 2.46 (m, 4H, $CH_2CH_2CN$), 3.63 (m, 4H, $C_5$, $CH_2$ and 2×$CH(CH_3)_2$), 3.77 (d, 6H, 2×$OCH_3$), 4.13 (m, 1H, $C_4$, H), 4.29 (m, 1H, $C_3$, H), 5.0 (m, 1H, $C_2$, H), 5.69 (m, 1H, $C_1$, H), 6.50 (m, 1H, $C_5$ H) and 6.75–7.72 (m, 14H, $C_6$ H and aromatic protons of DMT).

The $^{31}$P-NMR data in $CDCl_3$ was as follows: δ 147.98 and 148.56 ppm.

Example 2

Synthesis of 2'-trifluoroacetamido-3'-O-(4,4'-dimethoxytrityl)-2'-deoxyuridine-5'-succinate (hydroxyl/amino analog)

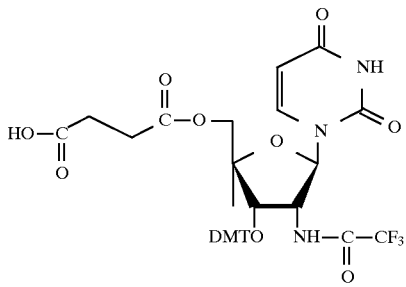

The following describes the synthesis of a succinate suitable for the preparation of a solid support which in turn can be utilized to prepare an oligonucleotide capable of being cleaved using cleaving reagent of the present invention. 2'-Amino-2'-deoxyuridine prepared according to literature procedures [J. Moffat et al., J. Org. Chem. 36, 250 (1971); F. Eckstein et al., J. Org. Chem. 42, 714 (1977)] (3.1 g, 12.76 mmole) was suspended in dry methanol (260 ml) and S-ethyl trifluoroacetate (2.5 ml, 19.67 mmole) was added. The mixture was stirred at room temperature for 2 hr and then left to stand at room temperature for 24 hr to obtain an homogeneous and clear solution. This solution was bubbled with nitrogen for 1 hr. The solvents were removed under reduced pressure to give 4 g of 2'-trifluoroacetamido-2'-deoxyuridine intermediate which was used without purification. This intermediate (1.5 g, 4.62 mmole) was dried by co-evaporation with dry pyridine (2×50 ml) and dissolved in dry pyridine (50 ml) containing imidazole (0.35 g, 5 mmole). Tert-butyldimethylsilyl chloride (0.75 g, 5 mmole) was added with stirring. The reaction mixture was stirred at room temperature for 16 hr. The solvent was removed under reduced pressure and the residue was dissolved in $CH_2Cl_2$ (100 ml) and washed with 5% sodium bicarbonate solution (2×50 ml) and dried over anhydrous sodium sulfate. Removal of solvent gave crude product which was purified on silica gel (60 g). Elution with $CH_2Cl_2$—MeOH (98/2, v/v) gave 5'-O-(tert-butyldimethylsilyl)-2'-trifluoroacetamido-2'-deoxyuridine (1.63 g, 78% yield).

5'-O-(tert-Butyldimethylsilyl)-2'-trifluoroacetamido-2'-deoxyuridine (1.5 g, 3.3 mmole) was dried by co-evaporation with dry pyridine (2×50 ml) and dissolved in dry pyridine (50 ml). Dimethoxytrityl chloride (1.725 g, 5.1 mmole) was added with stirring. The resultant reaction mixture was stirred overnight (16 hr). The reaction mixture was diluted with methanol (10 ml) and the solvents were removed under reduced pressure. The residue was dissolved in $CH_2Cl_2$ (100 ml), washed with 5% sodium bicarbonate solution (1×100 ml), brine (1×100 ml) and dried over anhydrous sodium sulfate. Removal of solvent gave the crude product which was purified on silica gel using $CH_2Cl_2$—MeOH (99:1, v/v) as eluted solvent. The fractions which contain the product were collected and evaporated to afford 2'-trifluoroacetamido-3'-O-(4,4'-dimethoxytrityl)-5'-O-(tert-butyldimethylsilyl)-2'-deoxyuridine (1.8 g, 72.29%).

2'-Trifluoroacetamido-3'-O-(4,4'-dimethoxytrityl-5'-O-(tert-butyldimethylsilyl)-2'-deoxyuridine (1.5 g, 1.98 mmole) was treated with (20 ml) of 1.0M tetrabutylammonium fluoride in THF at room temperature for 15 hr. The solvent was removed, the residue was dissolved in $CH_2Cl_2$ and applied to a silica gel column which was eluted with 400 ml portions of 0–3% methanol in CH$_2$Cl$_2$. The desired fractions were collected, evaporated to dryness and dried under vacuum to afford 2'-trifluoroacetamido-3'-O-(4,4'-dimethoxytrityl)-2'-deoxyuridine (0.9 g, 71% yield).

2'-Trifluoroacetamido-3'-O-(4,4'-dimethoxytrityl)-2'-deoxyuridine (0.64 g, 1 mmole), succinic anhydride (0.32 g, 2.55 mmole) and DMAP (0.7 g, 2.5 mmole) were dissolved in anhydrous pyridine (15 ml) and stirred at room temperature for 24 hr. The pyridine was evaporated under reduced pressure and the residue was co-evaporated with dry toluene (2×10 ml). The residue was dissolved in CH$_2$Cl$_2$ (10 ml) and precipitated at room temperature into rapidly stirring hexane (100 ml). The product was filtered and dried under vacuum to afford 2'-trifluoroacetamido-3'-O-(4,4'-dimethoxytrityl)-2'-deoxyuridine-5'-succinate.

Example 3

Synthesis of 2'-Trifluoroacetamido-3'-O-(4.4'-dimethoxytrityl)-2'-deoxyuridine-5'-O-(N,N'-diisopropyl)-β-cyanoethyl-phosphoramidite

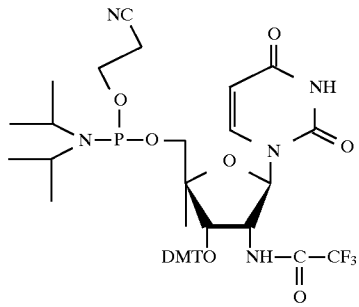

The following describes the synthesis of a phosphoramidite reagent useful in preparing an oligonucleotide reagent of the present invention. 2'-Trifluoroacetamido-3'-0-(4,41-dimethoxytrityl)-2'-deoxyuridine (0.64 g. 1 mmole) was dried by successive co-evaporation with pyridine, toluene and dissolved in dry THF (5 ml) containing N,N-diisopropylethylamine (0.85 ml, 4 mmole). To this solution, 0-cyano-ethylmonochloro-N,N-diisopropylphosphoramidite (0.5 ml, 2 mmole) was added dropwise using a syringe with constant stirring under argon atmosphere at room temperature over 5 minutes. After 90 min of stirring, the reaction mixture was evaporated to dryness and the residue was dissolved in ethyl acetate (50 ml), washed with 10% NaHCO$_3$ solution (2×50 ml) and dried over Na$_2$SO$_4$. Evaporated ethyl acetate under reduced pressure, the residue was purified using silica gel (preheated at 100°–120° C.) column chromatography to give 2'-trifluoroacetamido-3'-O-(4,4'-dimethoxytrityl)-2'-deoxyuridine-5'-O-(N,N-'-diisopropyl)-β-cyanoethyl-phosphoramidite.

Example 4

Synthesis of 2'-(Benzoylthio)-3'-O-(4,4'-dimethoxytrityl)-2'-deoxyuridine-5'-succinate (hydroxyl/thiol analog)

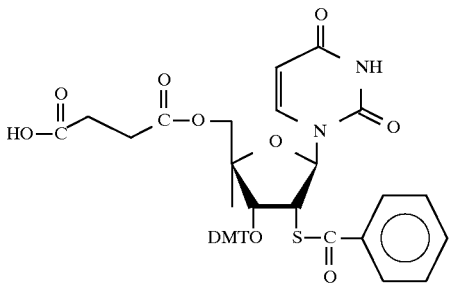

The following describes the synthesis of a suitable succinate reagent used to synthesize oligonucleotides which are capable of subsequent cleavage using the cleaving reagents and methods of the present invention. 2'-Deoxy-2'-mercaptouridine prepared according to the literature procedure [B. Reese et al., J. Chem. Soc., Perkin Trans 1, 969 (1990)] (2.6 g, 10 mmole) in dry pyridine (50 ml) was treated with 1,3-dichloro-1,1,3,3-tetraisopropyldisiloxane (3.13 ml, 10 mmole) under anhydrous conditions at room temperature. TLC showed complete reaction after 4 hr; solvent was removed in vacuo and the residual syrup was dissolved in ethyl acetate (50 ml). The solution was washed with 5% aqueous sodium bicarbonate (2×50 ml), dried over Na$_2$SO$_4$ and filtered, and the solvent was removed in vacuo. The crude 3',5'-O- (tetraisopropyldisiloxane-1,3-diyl) -2'-deoxy-2'-mercapto uridine was purified on silica gel column using CH$_2$Cl$_2$ as the eluting solvent.

3',5'-O- (Tetraisopropyldisiloxane-1,3-diyl) -2'-deoxy-2'-mercapto-uridine (5 mmole) was dissolved in dry pyridine (20 ml) containing DMAP (250 g, 2mmole). Benzoyl chloride (10 mmole) was added and the resultant mixture was stirred at room temperature for 5 hr. Solvent was removed in vacuo and the residue was dissolved in CH$_2$Cl$_2$ (50 ml), washed with 5% aqueous sodium bicarbonate and brine and dried over anhydrous sodium sulfate. The solvent was removed and the crude product 3',5'-O-tetraisopropyldisiloxane-1,3-diyl)-2'-deoxy-2'-(benzoylthio) uridine was purified on silica gel column chromatography.

3',5'-O- (Tetraisopropyldisiloxane-1,3-diyl) -2'-deoxy-2'-(benzoylthio) uridine (3.25 mmole) was dissolved in 25 ml 1.0M tetrabutylammonium fluoride in tetrahydrofuran. The solvent was removed under reduced pressure and the residue was taken in CH$_2$Cl$_2$ (10 ml) and purified on silica gel column chromatography to provide 21-deoxy-21-(benzoylthio) uridine.

2'-Deoxy-2'-(benzoylthio)uridine (2.75 mmole) was dried by co-evaporation with dry pyridine (2×20 ml) and dissolved in dry pyridine (50 ml) containing imidazole (5 mmole); tert-butyldimethylsilyl chloride (5 mmole) was added with stirring. The reaction mixture was stirred at room temperature for 16 hr. Solvent was removed under vacuo and the residue was dissolved in CH$_2$Cl$_2$ (100 ml), washed with 5% sodium bicarbonate solution (2×50 ml) and dried over anhydrous sodium sulfate. Removal of solvent gave crude product 5'-O-(tert-butyldimethylsilyl)-2'-deoxy- 2'-(benzoylthio) uridine which was purified on silica gel column chromatography.

5'-o-(tert-Butyldimethylsilyl)-2'-deoxy-2'-(benzoylthio) uridine (2.09 mmole) was dried by co-evaporation with dry pyridine (2×20 ml) and dissolved in dry pyridine (25 ml). Dimethoxytrityl chloride (3 mmole) was added with stirring. The reaction mixture was stirred at room temperature overnight (16 hr) and then diluted with methanol (10 ml). The solvents were removed under vacuo; the residue was dissolved in CH$_2$Cl$_2$ (100 ml), washed with 5% sodium bicarbonate (2×50 ml) and brine (50 ml) and dried over anhydrous sodium sulfate. Removal of solvent gave crude product 5'-O-(tert-butyldimethylsilyl)-3'-O-(4,4'-dimethoxytrityl)-2'-deoxy-2'-(benzoylthio) uridine which was purified on silica gel column chromatography.

5'-O-(tert-Butyldimethylsilyl)-3'-O-(4,4'-dimethoxytrityl)-2'-deoxy-2'-(benzoylthio)-uridine (1.4 mmole) was treated with 20 ml of 1.0M tetrabutylammonium fluoride in THF at room temperature for 16 hr. The solvent was removed and the residue was purified on silica gel column chromatography to provide 2'-(benzoylthio)-3'-O-(4,4'-dimethoxytrityl)-2'-deoxyuridine.

2'-(Benzoylthio)-3'-O-(4,4'-dimethoxytrityl)-2'-deoxyuridine (1 mmole), succinic anhydride (2.55 mmole) and DMAP (2.5 mmole) were dissolved in anhydrous pyridine (20 ml) and stirred at room temperature for 24 hr. The pyridine was evaporated under reduced pressure and the residue was co-evaporated with dry toluene (2×100 ml). The residue was dissolved in CH$_2$Cl$_2$ (15 ml) and precipitated at room temperature into rapidly stirred hexane (100 ml). The product was filtered and dried under vacuum to afford 2'-(benzoylthio)-3'-O-(4,4'-dimethoxytrityl)-2'-deoxyuridine-5'-succinate.

Example 5

Synthesis of 2'-(Benzoylthio)-3'-O-(4,4'-dimethoxytrityl) -2'-deoxyuridine 5'-O-(N,N'-diisopropyl)-β-cyanoethylphosphoramidite.

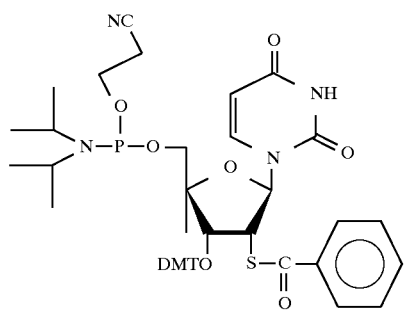

The following describes the synthesis of a phosphoramidite reagent useful in preparing an oligonucleotide synthesis reagent of the present invention. 2'-(Benzoylthio)-3'-O-(4,4'-dimethoxytrityl)-2'-deoxyuridine (1 mmole) was dried by successive co-evaporation with pyridine and toluene and dissolved in dry THF (5 ml) containing N,N-diisopropylethylamine (4 mmole). To this solution β cyanoethylmonochloro-diisopropylphosphoramidite (2 mmole) was added dropwise using a syringe with constant stirring under argon at room temperature over 5 minutes. After 60 min of stirring, the reaction mixture was evaporated to dryness and the residue was dissolved in ethyl acetate (50 ml) and washed with 10% NaHCO$_3$ solution (2×50 ml) and the organic layer was dried over Na$_2$SO$_4$. After evaporation of the ethyl acetate under reduced pressure, the residue was purified by silica gel (pre-heated at 100°–120° C.) column chromatography to provide 2'-(benzoylthio)-3'-O-(4,4'-dimethoxytrityl)-2'-deoxyuridine -5'-O-(N,N'-diisopropyl)-β-cyanoethyl-phosphoramidite.

Example 6

Synthesis of 2'(3')-O-(4,4'-dimethoxytrityl)-2'(3')-O-acetyl uridine-5'-succinate

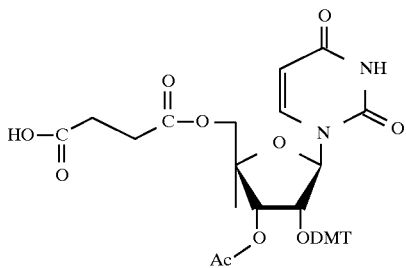

Uridine (10 g, 41 mmole), toluene-p-sulfonic acid monohydrate (2 g, 0.5 mmole) and trimethyl orthoacetate were stirred together at 20° C. for 20 hr. TLC revealed two products in the proportion of 4:1; no uridine was found. The reaction mixture was made slightly basic with methanolic MeONa, concentrated to an oil, dissolved in CH$_2$Cl$_2$ and purified by alumina column chromatography. The product was eluted with (CH$_2$Cl$_2$:MeOH, 96:4, v/v), the desired fractions were collected and evaporated under reduced pressure to afford 2',3'-O-methoxyethylidene uridine (8.8 g, 71.8% yield) as a colorless glass.

IR (KBr): u 1670 cm$^{-1}$ (s, C=O of ring amide), 2900–3600 cm$^{-1}$ (NH,OH).

$^1$H H-NMR (CDCl$_3$): δ 1.51 and 1.58 (2s, 3H, —CH$_3$), 3.14 and 3.29 (2s, 3H, OC$\underline{H}_3$), 3.58 (m, 2H, C$_{5'}$—C$\underline{H}_2$), 4.06 (m, 1H, C$_{4'}$—$\underline{H}$), 4.89–5.10 (m, 2H, C$_{2'}$—$\underline{H}$ and C$_{3'}$—$\underline{H}$), 5.63 (d, 1H, C$_5$—$\underline{H}$), 5.80 and 5.95 (2d, 1H, C$_{1'}$—$\underline{H}$), 7.77 (d, 1H, C$_6$—$\underline{H}$) and 11.42 (s, 1H, —NH).

To 5.2 g (18 mmole) of 2',3'-O-methoxyethylidene uridine in THF (100 ml), imidazole (4.9 g, 4 eq) was added followed by the addition of tert-butyldimethylsilyl chloride (5.4 g, 2 eq). The resultant reaction mixture was stirred at room temperature overnight (16 hr). After removing the solvent the residue was taken in CH$_2$Cl$_2$ (200 ml), washed with saturated solution of NaCl (200 ml), water and dried over Na$_2$SO$_4$. The solvent was removed under reduced pressure to afford almost pure 2',3'-O-methoxyethylidene-5'-O-(tert-butyldimethylsilyl) uridine (7.2 g, 99% yield) as semi solid which was used in the next step without further purification.

IR (Neat): 1650 cm$^{-1}$ (C=O of ring amide) and 3400–3600 cm$^{-1}$ (NH, OH).

$^1$H-NMR (CDCl$_3$): δ −0.005 (s, 6H—Si(C$\underline{H}_3$)$_2$), 0.82 (s, 9H, Si—(C$\underline{H}_3$)$_3$), 1.55 and 1.6 (2s, 3H, C$\underline{H}_3$), 2.79 and 2.87 (2s, 3H, —OC$\underline{H}_3$), 3.82 (m, 2H, C$_{5'}$—C$\underline{H}_2$), 4.22 (m, 1H, C$_{4'}$ $\underline{H}$), 4.65 (m, 2H, C$_2\underline{H}$, C$_3\underline{H}$), 5.64 (d, 1H, C$_{5\_}\underline{H}$), 6.0 (2d, 1H, C$_{1'}$—$\underline{H}$), 7.50 (d, 1H, C$_6$—$\underline{H}$) and 9.35 (br, 1H, NH).

To 8.0 g (27.58 mmole) of 2',3'-O-methoxyethylidene-5'-O- (tert-butyldimethylsilyl) uridine was added 80% aqueous acetic acid (20 ml) and the resultant mixture was stirred at room temperature for 30 min. After evaporation of the solvent the crude residue was purified by silica gel column chromatography using CH$_2$Cl$_2$/MeOH (97/3, v/v) as eluted solvent. The fractions which contain the desired compound were collected, evaporated and dried under vacuo to afford 2'(3')-O-acetyl-5'-O-(tert-butyldimethylsilyl)-uridine as a semi-solid (7.6 g, 68% yield).

IR (Neat): μ 1701 cm$^{-1}$ (s, br, C=O of acetyl group and ring amide).

$^1$H-NMR (CDCl$_3$): δ 0.07 (s, 6H, —Si(C$\underline{H}_3$)$_2$), 0.87 (s, 9H, —Si(C$\underline{H}_3$)$_3$), 2.03 and 2.10 (2s, 3H, COC$\underline{H}_3$), 3.87 (m, 2H, C$_{5'}$—CH$_2$), 4.33 (2m, 2H, C$_{3'}$ H and C$_{4'}$ H), 4.7 (m, 1H, C$_{2'}$ H), 5.65 (d, 1H, C$_5$H), 6.06 (2d, 1H, C$_{1'}$—H), 7.85 (d, 1H, C$_6$ H) and 10.18 (br, s 1H, NH).

2'(3')-O-Acetyl-5'1-O-(tert-butyldimethylsilyl)-uridine (4 g, 10 mmole) was dissolved in dry CH$_2$Cl$_2$ (50 ml). Collidine (4 ml) was added followed by addition of tetrabutylammonium perchlorate (5.13 g, 1.5 eq.) and dimethoxytrityl chloride (5.07 g, 1.5 eq.). The reaction mixture was stirred overnight (16 hr), washed successively with 2×50 ml of 5% aqueous NaHCO$_3$ solution and 2×50 ml of water. The organic layer was dried over anhydrous Na$_2$SO$_4$ and evaporated. The residue was purified by silica gel column chromatography; the column was packed with silica gel in 1% TEA/CH$_2$Cl$_2$ and the product eluted with CH$_2$Cl$_2$. The desired fractions were collected and evaporated to afford 2'(3')-O-acetyl-2'(3')-O-(4,4$^1$-dimethoxytrityl)-5'-O-(tert-butyldimethylsilyl)-uridine (4.8 g, 68% yield).

$^1$H-NMR (CDCl$_3$): δ 0.6 (m, 6H, Si(CH$_3$)$_2$), 0.88 (2s, 9H, Si(CH$_3$)$_3$), 2.22 (2s, 3H, COCH$_3$), 3.52 (m, 2H, C$_{5'}$—CH$_2$), 3.85 (2s, 6H, 2×OCH$_3$), 4.07 (m, 1H, C$_4$H), 4.26 (m, 1H, C$_{3'}$H), 5.08 (m, 1H, C$_2$H), 5.71 (2d, 1H, C$_1$H), 6.59 (2d, 1H, C$_5$H), 6.80–7.83 (m, 13H, aromatic H). and 8.74 (d, 1H, C$_6$ H).

2'(3')-O-Acetyl-2'(3')-O-(4,4'-dimethoxytrityl)-5'-O-(tert-butyldimethylsilyl)-uridine (1.5 g, 2.14 mmole) was dissolved in (15 ml) of 1.0M tetrabutylammonium fluoride in THF and the reaction mixture was stirred at room temperature for 15 hr. The solvent was evaporated and the residue was taken in CH$_2$Cl$_2$ (10 ml) and applied to a silica gel column which was eluted with 400 ml portions of 0–3% methanol in CH$_2$Cl$_2$. The desired fractions were collected, evaporated to dryness and dried under vacuum to afford 2'(3')-O-acetyl-2'(3')-O-(4,4'-dimethoxytrityl)-uridine (1 g, 79.4% yield).

$^1$H-NMR (CDCl$_3$): d 2.07 (d, 3H, —COCH$_3$), 3.61 (m, 2H, C$_{5'}$—CH$_2$), 3.83 (d, 6H, 2×OCH$_3$), 3.89 (m, 1H, C$_{4'}$ H), 4.44 (m, 1H, C$_{3'}$ H), 4.91 (m, 1H, C$_{2'}$ H) , 5.66 (m, C$_{1'}$ H), 6.03 (m, 1H, C$_5$ H), 6.75–7.43 (m, 13 H, aromatic H), and 7.49 (m, 1H, C$_6$ H).

2'(3')-O-Acetyl-2'(3')-O-(4,4'-dimethoxytrityl)-uridine (0.59 g, 1 mmole), succinic anhydride (0.32 g, 2.55 mmole) and DMAP (0.7 g, 2.5 mmole) were dissolved in anhydrous pyridine (10 ml) and stirred at room temperature for 24 hr. The pyridine was evaporated under reduced pressure, and the residue was co-evaporated with dry toluene (2×10 ml). The gummy residue was dissolved in CH$_2$Cl$_2$ (50 ml), washed with saturated NaCl solution (2×40 ml) and water (40 ml). The organic layer was dried over anhydrous Na$_2$SO$_4$ and then evaporated. The residue was dissolved in CH$_2$Cl$_2$ (10 ml) and precipitated at room temperature into rapidly stirred hexane (100 ml). The product was filtered and dried under vacuum to yield 2'(3')-O-(4,4'-dimethoxytrityl)-2'(3')-O-acetyl uridine-5'-succinate (0.4 g, 60% yield).

Melting point: 100°–115° C. (dec.).

$^1$H-NMR (CDCl$_3$): δ 2.10 (d, 3H, COCH$_3$), 2.50 (m, 4H, COCH$_2$CH$_2$CO), 2.96 (m, 2H, C$_{5'}$ CH$_2$), 3.75 (d, 6H, 2×OC H$_3$), 4.10 (m, 2H, C$_{4'}$ H and C$_{3'}$ H) , 4.23 (m, 1H, C$_{2'}$ H), 5.66 (d, 1H, C$_{1'}$ H), 6.32 (d, 1H, C$_5$ H), 6.74–7.41 (m, 14 H, DMT group and C$_6$ H) and 9.50 (s, 1H, COOH).

Example 7

Preparation of Hydroxy Derivatized Solid Support

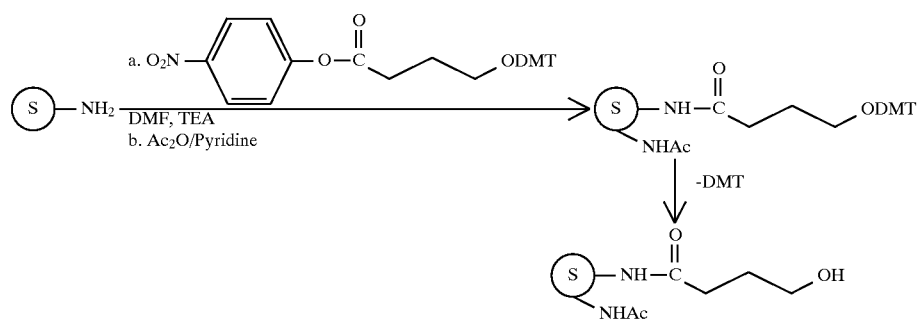

The following describes the preparation of a solid support for its subsequent reaction with a reagent suitable for the formation of an oligonucleotide synthesis reagent. To a suspension of Toyopearl AF-amino resin (1 g, amino=300 μmoles/g, TosoHaas, Philadelphia, Pa.) in 4 ml of dry DMF was added a solution of p-nitrophenol-4-[di-(p-methoxyphenyl) phenyl methyloxy]-butyrate (2.0 g, 0.4M) prepared according to the literature procedure [J. Haralambidis et al, Nucleic Acid Research 18, 493 (1989)] in 4 ml dioxane, followed by addition of TEA (2 ml). The reaction mixture was shaken at room temperature overnight (16 hr). The solid support was filtered, washed with DMF (5 ml), CH$_3$CN (2×5 ml), CH$_2$Cl$_2$ (2×5 ml) and diethyl ether (2×5 ml) and dried under vacuum for 3 hr. The resin was suspended in 10 ml of dry pyridine; DMAP (250 mg, 0.2M) was added, followed by addition of Ac$_2$O (2.5 ml, 2.5M) to cap unreacted amino groups, and the reaction mixture was shaken at room temperature for 5 hrs. The resin was filtered, washed with dry pyridine (10 ml), CH$_3$CN (10 ml) and diethyl ether (10 ml) and dried in vacuo for 2 hr. The hydroxy group loading of the solid support was found to be in the range of 200–250 μmoles/g as determined by measurement (at A$_{500}$ nm) to calculate the amount of dimethoxytrityl cation released.

A similar procedure was used for functionalization of CPG-LCAA and aminopropyl-CPG [H. Seliger and Groger, Nucleosides and Nucleotides 7, 773 (1988)] resins with hydroxy groups.

Example 8

Derivatization of CPG-solid support with uridine moiety via phosphate linkage

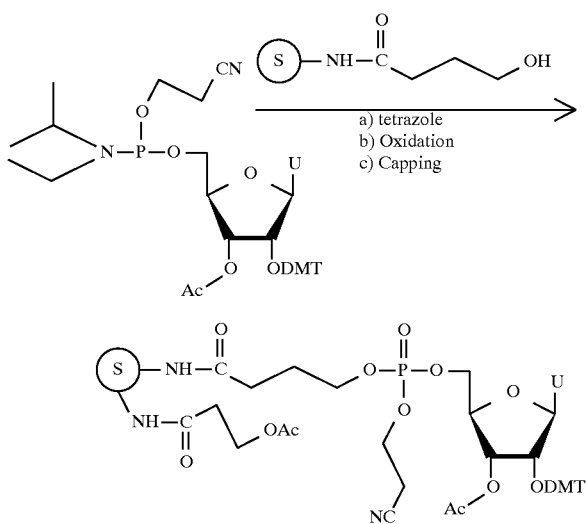

The following describes the preparation of a CPG solid support which can be used for the synthesis of oligonucleotides cleaved from the solid support in accordance with the present invention. CPG—OH solid support (500 mg, free OH=27 mmoles/g) from Example 7 was suspended in dry acetonitrile (3 ml). 2'(3')-O-acetyl-2'(3')-O-(4,4'-dimethoxytrityl)-uridine-5'-O-(β-cyanoethyl-N,N-diisopropyl)-phosphoramidite (39.4 mg, 0.05 mmole) was added, followed by the addition of 2 ml of a 0.5M solution of tetrazole in $CH_3CN$ and the reaction mixture was shaken at room temperature for 30 min. The solid support was filtered, washed with dry $CH_3CN$ (2×3 ml) and then suspended in 3 ml of $I_2$ solution (0.3% $I_2$ in THF/pyridine/water—93:5:2) and the reaction mixture was allowed to shake at room temperature for 30 min. The solid support was filtered, washed with THF (2×5 ml) and $CH_3CN$ (2×5 ml) and dried in vacuo for 1–2 hr. To the solid support was added 3 ml of 17% N-methylimidazole in THF, followed by addition of 3 ml of 10% $Ac_2O$, 10% lutidine, 80% THF v/v; the reaction mixture was shaken at room temperature for 30 min. The solid support was filtered, washed with $CH_3CN$ (2×5 ml) and diethyl ether (2×5ml) and dried in vacuo. Loading of the uridine moiety was found to be 20.2 μmoles/g as determined by measurement (at $A_{500}$ nm) of the amount of dimethoxytrityl cation released.

Example 9

Derivatization of Toyopearl (Fractogel 65M) resin with uridine moiety via Phosphate linkage Toyopearl (Fractogel 65M) resin (1 g, free OH=200 mmoles/g) from Example 7 was suspended in dry $CH_3CN$ (6 ml). 2'(3')-O-acetyl-2'(3')-O-(4,4'-dimethoxytrityl)-uridine-5'-O-(β-cyanoethyl-N,N'-diisopropyl)-phosphoramidite (39.4 mg, 0.05 mmole) was added, followed by addition of 2 ml of a 0.5M solution of tetrazole in $CH_3CN$ and the reaction mixture was shaken at room temperature for 30 min. The solid support was filtered, washed with dry $CH_3CN$ (2×6 ml) and then suspended in 6 ml of $I_2$ solution (0.3% $I_2$ in THF/pyridine/water—93:5:2) and the reaction mixture was allowed to shake at room temperature for 30 min. The solid support was filtered, washed with THF (2×6 ml), $CH_3CN$ (2×5 ml) and dried in vacuo for 2 hr. To the solid support was added 5 ml of (17% N-methylimidazole in THF), followed by addition of 5 ml of (10% $Ac_2O$, 10% lutidine, 80% THF, v/v) and the reaction mixture shaken at room temperature for 30 min. The solid support was filtered, washed with $CH_3CN$ (2×10 ml) and diethyl ether (2×5 ml) and dried in vacuo. Loading of the uridine moiety was found to be in the range of 45–55 μmoles/g as determined by measurement (at $A_{500}$ nm) of the amount of dimethoxytrityl cation released.

Example 10

Derivatization of Tentagel resin with uridine moiety via phosphate linkage

Tentagel-hydroxy resin (500 mg, free OH=200 mmoles/g) was derivatized with a uridine moiety following the procedure described in Examples 8 and 9. The loading of uridine moiety was found to be 17.6 μmoles/g as determined by measurement (at $A_{500}$ nm) of the amount of dimethoxytrityl cation released.

Example 11

Derivatization of Toyopearl (Fractogel AF-amino 65M) resin with uridine via phosphoramidate linker

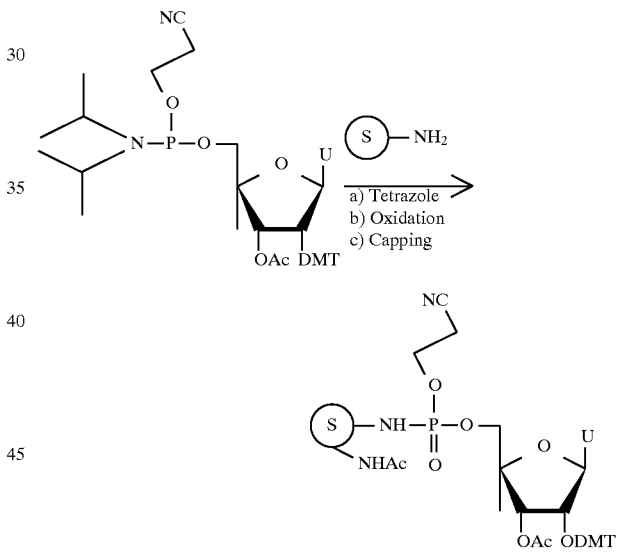

Toyopearl-AF-amino-65-resin (1 g, 300 mmoles/g amino group, TosoHaas, Philadelphia, Pa.) was suspended in dry $CH_3CN$ (6 ml). 2'(3')-O-acetyl-2'(3')-O-(4,4'-dimethoxytrityl)-uridine-5'-O-(P-cyanoethyl-N,N-diisopropyl)-phosphoramidite (39.4 mg, 0.05 mmole) was added, followed by addition of 2 ml of 0.5M solution of tetrazole in $CH_3CN$ and the reaction mixture was shaken at room temperature for 30 min. The solid support was filtered, washed with dry $CH_3CN$ (2×6 ml) and suspended in 6 ml of $I_2$ solution (0.3% $I_2$ in THF/pyridine/water—93:5:2) and the reaction mixture was shaken at room temperature for 30 min. The solid support was filtered, washed with THF (2×6 ml) and $CH_3CN$ (2×5 ml) and dried in vacuo for 2 hr. To the solid support was added 5 ml of 17% N-methylimidazole in THF, followed by addition of 5 ml of a solution of 10% $AC_2O$, 10% lutidine and 80% THF, v/v; the reaction mixture was shaken at room temperature for 30 min. The solid support was filtered, washed with $CH_3CN$ (2×10 ml) and diethyl ether (2×5 ml) and dried in vacuo. The loading of uridine moiety on the resin was determined by measuring trityl release of a small aliquot in 2.5% dichloroacetic acid in dichloromethane at 500 nm in a spectrophotometer. The loading in this example was 45 μmoles/g.

Example 12

Derivatization of CPG-LCAA resin with uridine moiety via phosphoramidate linker

CPG-LCAA resin (Sigma, 500 mg,~ 60 μmoles/g amino group) was suspended in dry $CH_3CN$ (3 ml). 2'(3')-O-acetyl-2'(3')-O-(4,4'-dimethoxytrityl)-uridine-5'-O-(O-cyanoethyl-N,N-diisopropyl)-phosphoramidite (39.4 mg, 0.05 mmole) was added, followed by addition of 2 ml of a 0.5M solution of tetrazole in $CH_3CN$, and the reaction mixture was shaken at room temperature for 30 min. The solid support was filtered, washed with dry $CH_3CN$ (2×3 ml) and then suspended in 5 ml of $I_2$ (0.3% $I_2$ in THF/pyridine/water—93:5:2) and the reaction mixture was shaken at room temperature for 30 min. The solid support was filtered, washed with THF (2×5 ml) and $CH_3CN$ (2×5 ml) and dried under vacuum for 2 hr. To the solid support was added 3 ml of 17% N-methylimidazole in THF, followed by addition of 3 ml of a solution of 10% $Ac_2O$, 10% lutidine and 80% THF, v/v; the reaction mixture was shaken a room temperature for 30 min. The solid support was filtered, washed with $CH_3CN$ (2×10 ml) and diethyl ether (2×5 ml) and dried in vacuo. The loading of uridine on the support was 8.1 μmoles/g as determined by $A_{500}$ nm of dimethoxytrityl cation released.

Example 13

Derivatization of Toyopearl (Fractogel) AF-amino-65M resin with uridine moiety via succinate ester linkage

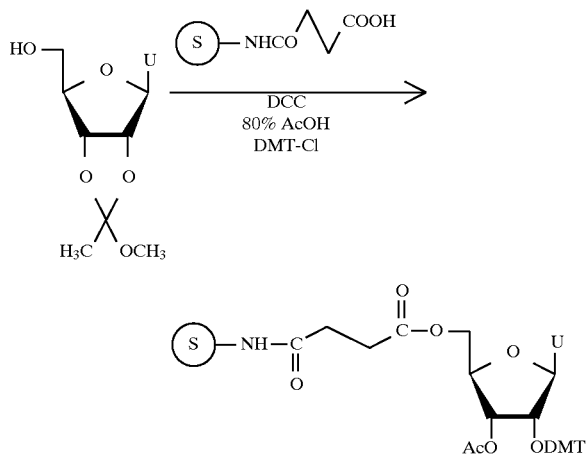

1 g of Toyopearl (Fractogel) AF-amino-650M (Amino groups=300 μmoles/g) was suspended in 10 ml of dry pyridine containing succinic anhydride (1 g, 1M) and N-methylimidazole (1 ml). The mixture was allowed to stand at room temperature for 16 hr. After filtration, the support was washed with aqueous pyridine, dry pyridine (10 ml), diethyl ether (10 ml) and dried in vacuo. A ninhydrin test was negative for free amino groups.

Succinylated support (1 g) was suspended in dry pyridine (10 ml) containing 2',3'-O-methoxyethylidine uridine (0.9 g, 3.12 mmole), DMAP (0.3 g, 2.46 mmole) and DCC (2.14 g, 10.37 mmole ) and the reaction mixture was shaken at room temperature for 48 hr. To this solution was added p-nitrophenol (1.8 g, 12.186 mmole) and the agitation was continued for another 20 hr. The reaction was quenched by the addition of morpholine (1 ml) and the shaking was continued for another 2 hr; this step is necessary to cap the unreacted carboxylic acid groups. The solid support was filtered, washed with pyridine (10 ml), MeOH (2×10 ml) and diethyl ether (10 ml) and dried in vacuo. The 2',3'-orthoester intermediate was hydrolysed to yield a mixture of 2',3'-acetates by treatment with 80% aqueous acetic acid (10 ml) at room temperature for 4 hr. After filtration the solid support was washed with MeOH (2×10 ml) and diethyl ether (10 ml) and dried in vacuo for 3 hr.

The solid support (1 g) was suspended in dry $CH_2Cl_2$ (10 ml), collidine (0.66 ml, 0.5M) was added followed by addition of tetrabutylammonium perchlorate (0.17 g, 0.05M) and dimethoxytrityl chloride (0.169 g, 0.05M). The reaction mixture was shaken at room temperature for 1 hr. The solid support was filtered, washed with $CH_2Cl_2$ (2×10 ml), MeOH (2×10 ml), diethyl ether (2×10 ml) and dried under vacuum for 3 hr. Loading of the solid support with uridine moiety was found to be 22.35 μmoles/g as determined by $A_{500}$ nm of dimethoxy trityl cation released.

Example 14

Derivatization of Tentagel-amino resin with uridine moiety via succinate ester linker

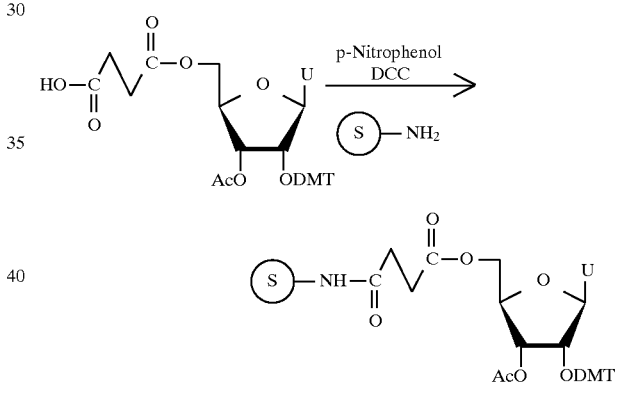

2'(3')-O-(4,4'-dimethoxytrityl)-2'(3')-O-acetyl uridine-5'-succinate (68.8 mg, 0.1 mmole) from Example 6 was dissolved in dry dioxane (4 ml) containing dry pyridine (0.4 ml) and p-nitrophenol (14 mg, 0.1 mmole). 1,3-Dicyclohexylcarbodiimide (DCC) (52 mg, 0.25 mmole) was then added and the reaction mixture was shaken at room temperature for 3 hr. The dicyclohexyl urea was removed by filtration and the supernatant was added to tentagel-amino resin (1 g, $NH_2$ group=220 m moles/g, RAPP Polymer Company, Germany) suspended in dry DMF (4 ml) followed by addition of triethylamine (2 ml) and the reaction mixture was shaken at room temperature for 6 hr. The solid support was filtered, washed extensively with DMF (2×10 ml) and diethyl ether (2×5 ml) and dried under vacuum for 1 hr. The solid support was resuspended in dry pyridine (10 ml), DMAP (250 mg, 0.2M) was added followed by the addition of acetic anhydride (2.5 ml, 2.5M) and the reaction mixture was shaken at room temperature for 16 hrs. The resin was filtered, washed with $CH_3CN$ (2×10 ml) and diethyl ether (2×10 ml) and dried in vacuo for 2 hr. The loading of the resin with uridine moiety was found to be 48.8 μmoles/g as determined by $A_{500}$ nm of dimethoxytrityl cation released.

23

Example 15

Derivatization of CPG—LCAA with uridine moiety via succinate ester linker

CPG (1 g, LCAA, Sigma, amino group=60 mmoles/g) was derivatized with a uridine moiety through a succinate ester linker following the procedures described in Examples 13 and to 14. Loading of the solid support with uridine was found to be 20.23 μmoles/g as determined by $A_{500}$ nm of dimethoxytrityl cation released.

Example 16

Derivatization of Toyopearl (Fractogel) 65 F-resin with uridine moiety via succinate ester linker

Fractogel 65 F-resin (5 g dry weight, TosoHaas, Philadelphia, Pa.) was suspended in dry $CH_3CN$ (50 ml); 1',1'-carbonyldiimidazole (8.1 g, to make 1M solution) was added and the reaction mixture was shaken at room temperature for 4 hr. The solid support was filtered on a sintered glass funnel and washed with dry $CH_3CN$ (2×50 ml) and then resuspended in dry $CH_2Cl_2$ (50 ml). 1,12-diaminododecane (10 g, to make 1M solution) was added and the resultant mixture was shaken at room temperature overnight (16–20 hr). n-Propylamine (4.1 ml, to make 1M solution) was added to the above mixture and the solution was shaken for an additional one hour. The resin was filtered and washed successively with dry $CH_2Cl_2$ (5×50 ml), acetone (5×50 ml) and $CH_3CN$ (5×20 ml), the last filtrate wash showing a negative ninhydrin test; the resin was then washed with diethyl ether (2×20 ml) and dried under vacuum for about 3 hr. The amino group content on the solid support was found to be in the range of 300–400 μmoles/g as determined by picric acid assay. [J. M. Stewart & J. D. Young, Solid Phase Peptide Synthesis, Pierce Chemical Company, 107 (1984)]. The solid support (1 g) was then reacted with succinic anhydride following the procedure described in Example 13. Succinylated resin (1 g) was then functionalized with the uridine derivative following the procedure of Example 13. The solid support was reacted with dimethoxytrityl chloride following the procedure of Example 13. Loading of the solid support with uridine moiety was found to be in the range of 20–25 mmoles/g as determined by $A_{500}$ nm of dimethoxytrityl cation released.

Example 17

Derivatization of Toyopearl (Fractogel) 65F-resin with uridine moiety through carbamate (urethane) linker

Functionalization of Fractogel 65F-resin (5 g, dry weight) with 1,12-diaminododecane was carried out following the procedure of Example 16. The amino group content on the solid support was found to be 330 μmoles/g as determined by picric acid assay.

The solid support (1 g) was suspended in dry $CH_2Cl_2$ (20 ml); p-nitrophenyl chloroformate (4.02 g, to make 1M solution) was added followed by the addition of collidine (3.95 ml, to make 1.5M solution) and the reaction mixture was shaken at room temperature overnight (16–20 hr). The solid support was filtered, washed with dry $CH_2Cl_2$ (5×20 ml) and dried in vacuo for 2 hr.

The solid support (1 g) was then suspended in dry $CH_2Cl_2$ (10 ml). 2',3'-O-methoxyethylidene uridine (3 g, to make 1M solution) was added followed by the addition of TEA (1.52 ml, to make 1M solution) and the reaction mixture was shaken at room temperature for 24 hr. The reaction mixture was quenched by addition of n-propylamine (0.82 ml, to make 1M solution) and the shaking was continued for another 1 hr. The solid support was filtered, washed with $CH_2Cl_2$ (2×10 ml), $CH_3OH$ (2×10 ml) and diethyl ether (2×10 ml) and dried under vacuum for 2 hr. The 2',3'-orthoester intermediate was hydrolysed to yield a mixture of 2', 3'-acetates acetates by treating the solid support with 80% aqueous acetic acid (10 ml) at room temperature for 4 hr. The solid support was filtered, washed with $CH_3OH$ (2×10 ml) and diethyl ether (10 ml) and dried in vacuo for 3 hr.

The solid support (1 g) was then suspended in dry $CH_2Cl_2$ (10 ml) and collidine (0.66 ml, 0.05M) was added, followed by the addition of tetrabutylammonium perchlorate (0.17 g, 0.05M) and dimethoxytrityl chloride (0.169 g, 0.5M). The reaction mixture was shaken at room temperature for 1 hr. The solid support was filtered and washed with $CH_2Cl_2$ (2×10 ml), $CH_3OH$ (2×10 ml) and diethyl ether (2×10 ml) and dried under vacuum for 3 hr. Loading of the solid support with uridine moiety was found to be in the range of 20–30 mmoles/g as determined by $A_{500}$ nm of dimethoxytrityl cation released.

Example 18

Synthesis of 51 mer

The following describes the synthesis of an oligonucleotide and the subsequent cleaving of the oligonucleotide using a cleaving reagent of present invention.

An oligonucleotide of sequence: 5'TCC.ATG.GCA.AC-T.GTC.AAG.GCA.CTG.GCT.CGT.AGC.CTA.CTG.GC-T.TGA.CCG.TAA3' (SEQ ID NO: 1) was assembled on the solid support of Example 15, using an Oligo-1000 DNA Synthesizer (Beckman Instruments, Brea, Calif.) and a standard synthetic protocol. After removing the last trityl group, the oligomer having a 3'-terminal uridine moiety was cleaved from the solid support by contacting the solid support with a solution of $CH_3NH_2/Me_3N$ at room temperature for 5 minutes. The solution was a 1:1, v/v, of 40% aqueous methyamine and 24 wt % aqueous trimethylamine. After removing the cleaved oligonucleotide from the solid support, the methylamine/trimethylamine solution containing the cleaved oligonucleotide was heated at 65° C. for 3 hr. The reagent was evaporated to dryness using a speed vac concentrator. The residue was dissolved in double distilled water (200 ml) and the product was analyzed by capillary gel electrophoresis. The P/ACE electropherogram revealed a high quality product which was identified by comparing its elution time with same sequence independently synthesized on a conventional CPG-A support.

Example 19

Synthesis of 101 mer and 35 mer

The following describes the synthesis an oligonucleotide utilizing an oligonucleotide synthesis reagent of the present invention and cleaving reagents of the present invention.

An oligonucleotide of sequence 5'AAC.GTC.GGT.AAC.GTA.CAC.GGT.AGC.TAC.GG-A.CAC.CGT.GGC.AAT.ACG.ACA.GGT.AAC.CTG.TG-G.AAC.GTA.CAC.GGA.AGA.GAC.TAG.GGA.TGG.GA-G.TAC.GGA.TGG .GT3' (SEQ ID NO: 2) was assembled on the solid support of Example 11, using an Oligo 1000 DNA Synthesizer and standard synthetic protocol. After removing the last trityl group the solid support was dried and placed in a screw cap vial with ~300 ml of $MeNH_2/Me_3N$ (1:1, v/v as described in Example 18)) and heated at 65° C. (water bath) for 90 min. The reagent (MeNH$_2$/$_3$N) was carefully decanted to another vial and evaporated to dryness using a speed vac concentrator. The residue was dissolved in double distilled water (500 ml) and the total A$_{260}$ nm was calculated. The product was analyzed by capillary gel electrophoresis. The P/ACE electropherogram revealed a good quality product. This product was identified by comparing its elution time with the same sequence independently synthesized on a regular CPG—T support.

A 35 mer of the sequence 5'GAT.GCC.AGT.TCG.GT-C.ATA.CAC.GTA.GTA.CTA.CGA.CC$^{3'}$ (SEQ ID NO: 3) was synthesized on the solid support of Example 11 and analyzed by capillary electrophoresis and by reverse phase HPLC as 5'-DMT oligonucleotides.

Example 20

Synthesis of 10mer oligoribonucleotide (RNA)

0.2 μmole (loading 20 μmoles/g) of CPG support, derivatized as described in Example 15, was placed in a column and a 10 mer of sequence 5'UCC.GAU.AGC.U$^{3'}$ (SEQ ID NO: 4) was synthesized on an Oligo-1000 automated synthesizer using the procedures of Scaringe et al., Nucleic Acid Research 18, 5433–5411 (1990). The coupling time for RNA synthesis was 12 minutes. The last DMT group was left on the oligonucleotide. After the synthesis, the RNA was deprotected and cleaved from the support using a 1:1 v/v solution of CH$_3$NH$_2$/(CH$_3$)$_3$N for 4 hours at 65° C. The 1:1 solution was prepared using a 40% w/v aqueous methylamine solution and a 23%–25% by wt. aqueous trimethylamine solution. The 2'-protecting group was removed using 1.0M tetrabutylammonium fluoride in THF for 15 hrs at room temperature. The oligoribonucleotide was desalted using a Nap-10 column (Pharmacia LKB Biotechnology, Piscataway, N.J.). The resultant product after HPLC purification with the DMT group still in place was chemically and physically indistinguishable from a 10 mer synthesized using a commercially available CPG support.

HPLC: retention time 21.40 minutes. Conditions: C18 Microsorb MV (Rainin) 5 m particles, 4.6 mm×25 cm. Bottle A: 0.1M ammonium acetate (pH 6.9); Bottle B: Acetonitrile. Flow rate: 1 ml/min., 0–25 min gradient to 50% B, 25–27 min at 50% B. 27030 min gradient to 0% B, 30–32 min at 0% B.

Example 21

Synthesis of 21 mer RNA

The following describes the synthesis of an oligonucleotide RNA using an oligonucleotide synthesis reagent of the present invention and cleaving reagents of the present invention.

0.2 mmole (loading 8.09 mmoles/g) of CPG support, derivatized as described in Example 12 was placed in a column and a 21 mer of sequence 5'CUG.GAC.AC-U.AGU.CCG.ACU.GCU3' (SEQ ID NO: 5) was synthesized on an Oligo-1000. The coupling time was 12 minutes. Cleavage and deprotection was performed using the MeNH$_2$/Me$_3$N (1:1, v/v) described in Example 20 for 2 hrs at room temperature. The 2'-protecting group was removed using 1.0M tetrabutylammonium fluoride in THF for 15 hrs at room temperature. The oligoribonucleotide was desalted using Sep-Pak (C18 cartridges from Millipore). Samples were lyophilized and analyzed by capillary electrophoresis on a Beckman P/ACE 2000. The capillary gel column was a Beckman Instruments U100 P Urea Gel column, having a 37 cm overall length. A Beckman Tris-Borate, 7M Urea Buffer Gel Buffer Kit was used according to manufacturer's instructions. The absorbences of the oligoribonucleotides were in the range of 1.0 to 2 OD260 nm/ml, depending upon the quality and length of oligoribonucleotide. Injection was at 10 kV for 5 sec, while separation was at 11 kV for 30–60 min, depending upon the length.

Example 22

Synthesis of Phosphorothioates

The following describes the synthesis of phosphorothioates and their subsequent cleaving by a method of the present invention.

A 25 mer phosphorothioate of sequence 5'AGT.CAG.T-CA.GTC.AGT.CAG.TCA.GTC.T$^{3'}$ (SEQ ID NO: 6) was synthesized on the solid support prepared in Example 15. The synthesis was performed using 0.2 μmole scale (loading 20 μmoles/g) on an Oligo-1000. After the synthesis, the oligo was cleaved and deprotected using the MeNH$_2$/Me$_3$N (1:1) solution prepared in Example 20 for 4 hrs at 65° C. The sample was analyzed by HPLC and CE. HPLC retention time for the phosphorothioate having final DMT in place was 17.23 minutes under the conditions described in Example 20. CE retention time was 27.40 minutes for the phosphorothioate with the final DMT removed; the conditions were the same as in Example 21. The resultant product was chemically and physically indistinguishable from a 25 mer synthesized on commercially available CPG support.

Example 23

Synthesis of Phosphorothioate

The following describes the synthesis of a phosphorothioate utilizing an oligonucleotide synthesis reagent of the present invention and a cleaving reagent of the present invention.

Following the procedure described in Example 22, an oligophosphorothioate of sequence 5'AGT.CAG.TCA.GT-C.AGT.CAG.TCA.GTC.T$^{3'}$ (SEQ ID NO: 6) was synthesized on the solid support prepared in Example 12. Cleavage and deprotection was carried out with the MeNH$_2$/Me$_3$N (1:1 v/v) reagent of Example 20 for 2 hrs at room temperature. HPLC retention time of cleaved phosphorothioate having the final DMT in place was 17.22 minutes. The CE retention time for the phosphorothioate having the final DMT removed was 26.64. The conditions were the same as in Example 20 for HPLC and Example 21 for CE.

Example 24

Enzyme Digestion of crude Hetero 15 mer synthesized on CPG—Universal solid support A 15 mer of sequence 5'GAC.CAG.TAC.TCA.CGA$^{3'}$ (SEQ ID NO: 7) was assembled on CPG solid support from Example 15 and on a regular CPG—A support having a succinyl linker. After removing the last DMT protecting group, the oligomer synthesized on the solid support of Example 15 was cleaved and deprotected with the CH$_3$NH$_2$/Me$_3$N (1:1 v/v) solution prepared in Example 20 at 65° C. for 4 hr the oligomer synthesized on regular CPG—A support was cleaved and deprotected with ammonia at 65° C. for 3 hr.

The crude oligomers were subjected to enzyme digestion using phosphodiesterase I (Sigma) reconstituted with 5 ml of 40 nM Tris, 10 nM $MgCl_2$, pH 7.5 (using 0.01 U per assay) and alkaline phosphatase (Sigma) from *E. coli* 200 u/1.8 ml (using 0.2 u per assay). To 1–2 $OD_{260}$ nm of oligonucleotide was added 25 ml of phosphodiesterase and 2 ml of alkaline phosphatase and the mixture incubated at room temperature for 30 min to 2 hrs. The sample was injected as such on a reverse phase HPLC C-18 column.

HPLC column: C18 Ultrasphere (Beckman) 5 m particles, 4.6 mm×25 cm.

Buffer A: 0.1M ammonium acetate

Buffer B: Acetonitrile

Program: Flow rate 1 ml/min.

0–20 min gradient to 15% B

20–25 min gradient to 25% B

25–27 min gradient to 50% B

27–30 min at 50% B

30–35 min at 0% B

Table I shows that there is a close agreement between the theoretical and the observed values of the oligonucleotides synthesized on the solid support of Example 15 (Universal CPG) and on a regular CPG A-support.

TABLE I

| | | Observed Value | |
|---|---|---|---|
| Theoretical value | | CPG-A support | Example 15 |
| A | 5 | 5.17 | 5.10 |
| C | 5 | 4.64 | 5.13 |
| G | 3 | 3.18 | 2.95 |
| T | 2 | 2.00 | 1.82 |

Example 25

Nucleoside composition analysis of 35 mer

A 35 mer of sequence 5'GAT.GCC.AGT.TCG.GTC.AT-A.CAC.GTA.GTA.CTA.CGA.CC3' (SEQ ID NO:3) was synthesized on 0.2 µmole (loading 20 µmoles/g) of CPG—T and on the prepared as described in Example 15. An Oligo-1000 DNA Synthesizer was utilized. After synthesis, cleavage and deprotection was done using the $MeNH_2/Me_3N$ (1:1, v/v) as described in Example 20 for 4 hrs at 65° C. 1 $OD_{260}$ nm of sample was taken and mixed with 25 ml of snake venom phosphodiesterase and 2 ml of alkaline phosphatase. The mixture was kept at room temperature for 30 minutes and injected onto an HPLC column using the conditions described in Example 24. The results are reported in Table II.

TABLE II

| | Observed value | |
|---|---|---|
| Theoretical value | Example 15 Support | T-CPG support |
| A 9 | 9.14 | 8.65 |
| C 9 | 8.63 | 9.26 |
| G 8 | 8.20 | 8.90 |
| T 9 | 9.02 | 8.91 |

Example 26

Reusable support for oligodeoxyribonucleotides/oligoribonucleotide synthesis

After assembling oligonucleotide on the solid support synthesized according to the procedures described in Example 11, the oligonucleotide was cleaved from the solid support using $MeNH_2/Me_3N$ (1:1, v/v) prepared as described in Example 20 at 65° C. for 2 hr. The solid support was washed with distilled water (1 ml) and treated with $[Co)triethylenetetramine(OH)H_2O]^{+2}$ as described in Y. Matsumoto et al., Chemistry Letters 427 (1990). To a 0.05M solution of $[Co(triethylenetetramine)Cl_2]Cl$ (15.57 mg/1 ml water) prepared according to the literature procedure [J. Chin and X. Zou, Can. J. Chem. 65, 1882 (1987); J. Chin and X. Zou, J. Amer. Chem. Soc. 110, 223 (1988)] 1.5 equivalents of NaOH (0.075M, 3 mg/ml water) was added. After 10 min, the pH of the solution was adjusted to pH 7.0 by addition of 1N HCl. This solution was added to the above solid support and shaken at room temperature for 30 min. This step hydrolyzes the cyclic phosphate to cis-diol. The solid support was filtered, washed with distilled water (2 ml), $CH_3CN$ (2×2ml) and diethyl ether (1 ml) and dried in vacuo.

The solid support was then suspended in 1 ml of dry $CH_2Cl_2$. Collidine (1.3 ml, 0.001M) was added, followed by the addition of tetrabutylammonium perchlorate (0.34 mg, 0.001M) and dimethoxytrityl chloride (0.338 mg, 0.001M). The reaction mixture was shaken at room temperature for 15 min. The solid support was filtered, washed with $CH_2Cl_2$ (1 ml), $CH_3OH$ (1 ml), diethyl ether (1 ml) and dried under vacuum for 1 hr.

The solid support was then suspended in dry pyridine (1 ml). DMAP (1.25 mg, 0.001M) was added, followed by the addition of acetic anhydride (12.5 ml, 0.0125M) and the reaction mixture was shaken at room temperature for 15 min. The solid support was filtered, washed with dry $CH_3CN$ (1 ml) and diethyl ether (1 ml) and dried under vacuum for 30 min.

Example 27

Synthesis of 2',3'-O-methoxyethylidene-uridine-5'-O-(N,N-diisopropyl)-β-cyanoethyl-phosphoramidite

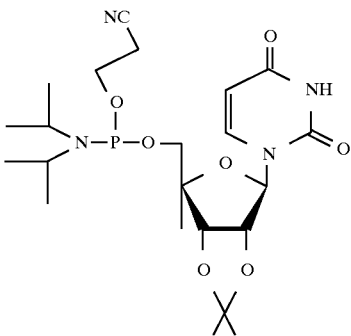

The following describes the synthesis of a reagent and its subsequent reaction with amino functionalized solid support to provide an oligonucleotide synthesis reagent of the present invention.

2',3'-O-Methoxyethylidene uridine (0.58 g, 2 mmole) was dissolved in anhydrous THF (10 ml). Diisopropylamine (1.4 ml, 8 mmole) was added at room temperature followed by the addition of β-cyanoethylmonochloro-N,N-diisopropylphosphoramidite (0.9 ml, 4 mmole) with magnetic stirring. After 1 hour of stirring the solvent was evaporated at 30° C. under vacuo. The crude product was redissolved in ethyl acetate (50 ml), washed with water and dried over anhydrous sodium sulfate. After removing the solvent under reduced pressure, the residue was taken in ethyl acetate (10 ml) and passed through a column of silica gel (pre heated at 100°–120° C.) packed with ethyl acetate/diisopropylamine (95/5, v/v) and eluted with ethyl acetate. The desired fractions were collected, evaporated and dried under high vacuum to afford 2',3'-O-methoxyethylidene-uridine-5'-O-(N,N-diisopropyl)-β-cyanoethyl-phosphoramidite (0.55 g, 56% yield).

IR (Kbr pellet): u 1700 cm$^{-1}$ (C=O of ring amide), 2250 cm$^{-1}$ (C≡N), and 2900 cm$^{-1}$ (s, NH).

$^1$H NMR (CDCl$_3$): δ 1.10–1.28 (m, 12H, 2×CH(CH$_3$)$_2$), 1.62 and 1.68 (2s, 3H, COCH$_3$), 2.66 and 2.76 (2t, 4H, CH$_2$CH$_2$), 3.27 and 3.40 (2s, 3H, OCH$_3$), 3.55 (m, 2H, 2×N—CH(CH$_3$)$_2$), 3.88 (m, 2H, C$_5'$—CH$_2$), 4.15 (m, 1H, C$_4'$—H), 4.97 (m, 2H, C$_2$H, C$_3$H), 5.76 (m, 1H, C$_5$—H), 6.03 (d, 1H, C$_1$—H) and 7.54 (d, 1H, C$_6$—H).

2',3'-isopropylideneuridine-5'-O-(N,N-diisopropyl)-β-cyanoethyl-phosphoramidite was also prepared by a similar procedure.

The above synthesized phosphoramidite compounds were used to prepare oligonucleotide reagents of the present invention by attaching the phosphoramidites to a variety of solid supports to form a phosphoramidate linkage between an oligonucleotide synthesis site and the solid support. To accomplish this CPG and Fractogel having surface amino groups were reacted with the phosphoramidites. After treating this reaction product with 80% aqueous acetic acid the 2',3'-O-cyclic orthoester functionality opened to provide the oligonucleotide synthesis reagent of Example 11.

Example 28

Synthesis of 1,2-O-methoxybenzylidene glycerol

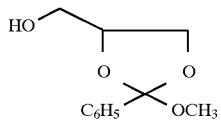

The following describes the synthesis of a glycerol type compound for use in preparing an oligonucleotide reagent suitable for synthesizing oligonucleotides which are subsequently cleaved from the solid support with cleaving reagents of the present invention.

Glycerol (5.61 g, 61 mmole) was suspended in THF (200 ml) containing trimethyl orthobenzoate (22.8 g, 125 mmole) and anhydrous benzenesulfonic acid (0.6 g). After stirring at 25° C. for 1 hr with exclusion of moisture, the solution became clear. TLC showed complete conversion of the starting material into a new compound with higher $R_f$. The reaction mixture was quenched by the addition of methanolic NaOCH$_3$ (1M, 5 ml) and the solvents were removed under reduced pressure The oily residue was dissolved in CH$_2$Cl$_2$ and purified by alumina column chromatography. The product was eluted with CH$_2$Cl$_2$/MeOH (99/1, v/v) and the desired fractions were collected and evaporated under reduced pressure to afford the title compound as a colorless oily material (9.6 g, 74.9% yield).

$^1$H NMR (CDCl$_3$): δ 3.69 (m, 4H, 2—CH$_2$), 4.0 (t, 1H, CH), 4.3 (d, 3H. —OCH$_3$), 7.37–8.0 (m, 5H, aromatic).

The above prepared compound was used to prepare a oligonucleotide synthesis reagent by reacting it with a standard succinylated CPG and Fractogel solid supports. Subsequently contacting the reacted solid support with 80% aqueous acetic acid at room temperature provide a reagent having a glycerol moiety attached to the support through an ester linkage.

Example 29

The following demonstrates the unexpected cleaving properties associated with various cleaving reagents of the present invention.

The 35-mer prepared using the solid support describe in Example 25 was utilized to study the effectiveness of various cleaving reagents. The solid support containing the synthesized 35-mer was contacted with each cleaving reagent for 30 minutes at 65° C. and the % of oligonucleotide actually detached from the solid support was measured.

The results of the cleaving reaction are shown in Table III.

TABLE III

| Cleaving Reagent | % of Synthesized Oligonucleotide Detached from the Vicinal Diol |
| --- | --- |
| NH$_4$OH | 23% |
| CH$_3$NH$_2$ (40% aqueous) | 41% |
| CH$_3$NH$_2$/(CH$_3$)$_3$N (1:1) | 62% |
| CH$_3$NH$_2$/(CH$_3$CH$_2$)$_3$N/CH$_3$CH$_2$OH (1:1:0.2) | 58% |
| CH$_3$NH$_2$/N-methylpyrrolidine (1:1) | 58% |
| CH$_3$NH$_2$/Dimethylamine (1:1) | 56% |
| CH$_3$NH$_2$/Diisopropylethylamine (1:1) | 52% |
| CH$_3$NH$_2$/Diisopropylamine (1:1) | 45% |
| CH$_3$NH$_2$/(CH$_3$)$_3$N (9:1) | 46% |
| CH$_3$NH$_2$/(CH$_3$)$_3$N (1:9) | 30% |
| CH$_3$NH$_2$/(CH$_3$)$_3$N (3:1) | 51% |
| CH$_3$NH$_2$/(CH$_3$)$_3$N (1:3) | 40% |
| CH$_3$NH$_2$/(CH$_3$)$_3$N (1:2) | 48% |
| CH$_3$NH$_2$/(CH$_3$)$_3$N (1:4) | 40% |
| CH$_3$NH$_2$/(CH$_3$)$_3$N (99:1) | 44% |
| CH$_3$NH$_2$/(CH$_3$)$_3$N (95:5) | 45 |
| NH$_4$OH/(CH$_3$)$_3$N (1:1) | 30% |
| NH$_4$OH/( CH$_3$CH$_2$)$_3$N/CH$_3$CH$_2$OH (1:1:0.2) | 30% |

Solutions containing NH$_4$OH, CH$_3$NH$_2$, (CH$_3$)$_3$N, (CH$_3$)$_2$NH, were prepared from about 29 wt %, 40 wt %, about 24 wt %, and 40 wt. % aqueous solutions, respectively.

In accordance with the present invention, even small amounts of stronger bases such as trimethylamine and triethylamine accelerate the cleaving kinetics. This is demonstrated by the cleaving data obtained with a solution prepared of 99 parts 40% aqueous methylamine and 1 part 24 wt % aqueous trimethylamine (39.6% methylamine and 0.24% trimethylamine) compared with the data for 40 wt % methylamine (44% cleavage after 30 minutes compared with 41% cleavage after 30 minutes(. The fact that CH$_3$NH$_2$/(CH$_3$)$_3$N (99:1) gives much faster kinetics than CH$_3$NH$_2$/(CH$_3$)$_3$N (1:9) illustrates that methylamine also plays a significant role in the cleaving reaction. The ethyl alcohol noted above is utilized in the cleaving reagent in order to render the solutions miscible.

As mentioned supra, ammonia, methylamine and trimethylamine are gases at standard temperature and pressure. They are readily available in aqueous solutions which were the forms utilized in preparing the solutions mentioned above. The solutions used were 40 wt % aqueous methylamine and 23–25 wt % trimethylamine. Thus, the 1:1 methylamine:trimethylamine are about 20 wt % methylamine and in about 12 wt % trimethylamine. Similarly, the ammonium hydroxide NH$_4$OH was prepared using concentrated ammonium hydroxide or about 28 wt % to 30 wt %. The above described cleaving reagent containing methylamine and trimethylamine vary in concentrations of from about 0.4 wt. % to 39.6 wt. % methylamine and from about 0.24 wt. % to about 22.5 wt. % trimethylamine.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:1:

```
TCCATGGCAA CTGTCAAGGC ACTGGCTCGT AGCGTACTGG CTTGACCGTA A          51
```

( 2 ) INFORMATION FOR SEQ ID NO:2:

( i ) SEQUENCE CHARACTERISTICS:
        ( A ) LENGTH: 101 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:2:

```
AACGTCGGTA ACGTACACGG TAGCTACGGA CACCGTGGCA ATACGACAGG            50

TAACCTGTGG AACGTACACG GAAGAGACTA GGGATGGGAG TACGGATGGG T          101
```

( 2 ) INFORMATION FOR SEQ ID NO:3:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:3:

```
GATGCCAGTT CGGTCATACA CGTAGTACTA CGACC                            35
```

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear

```
        ( i i ) MOLECULE TYPE: RNA (genomic)

( i i i ) HYPOTHETICAL: YES ( i v ) ANTI-SENSE: NO ( x i ) SEQUENCE DESCRIPTION: SEQ ID NO:4:

U C C G A U A G C U                                                                                    1 0

( 2 ) INFORMATION FOR SEQ ID NO:5:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: RNA (genomic)

( i i i ) HYPOTHETICAL: YES ( i v ) ANTI-SENSE: NO ( x i ) SEQUENCE DESCRIPTION: SEQ ID NO:5:

C U G G A C A C U A   G U C C G A C U C G   U                                                          2 1

( 2 ) INFORMATION FOR SEQ ID NO:6:

( i ) SEQUENCE CHARACTERISTICS:
                ( A ) LENGTH: 25 bases
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( i v ) ANTI-SENSE: YES ( x i ) SEQUENCE DESCRIPTION: SEQ ID NO:6:

A G T C A G T C A G   T C A G T C A G T C   A G T C T                                                  2 5

( 2 ) INFORMATION FOR SEQ ID NO:7:

( i ) SEQUENCE CHARACTERISTICS:
                ( A ) LENGTH: 15 Bases
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:7:

G A C C A G T A C T   C A C G A                                                                        1 5
```

What is claimed is:

1. An oligonucleotide cleaving reagent consisting of:

A) about one to 99 parts of a first aqueous solution consisting of about 40 wt. % methylamine; and
   B) about one to four parts of a second aqueous solution selected from the group consisting of;
      1) about 40 wt. % dimethylamine, and
      2) about 24 wt. % trimethylamine.

2. The oligonucleotide cleaving reagent of claim 1 wherein said first compound is methylamine.

3. An aqueous oligonucleotide cleaving reagent consisting of about 8 wt. % to about 39.6 wt. % methylamine and about 0.24 wt. % to about 19.2 wt. % trimethylamine.

4. The aqueous oligonucleotide cleaving reagent of claim 3 further including a lower alkyl alcohol.

5. The oligonucleotide cleaving reagent of claim 1 wherein said second aqueous solution is trimethylamine.

6. The aqueous oligonucleotide cleaving reagent of claim 3, comprising about 20 wt. % of methylamine and about 12 wt. % of trimethylamine.

7. An aqueous oligonucleotide cleaving reagent comprising:
   A) a first compound selected from the group consisting of;
      1) methylamine, and
      2) ammonium hydroxide; and
   B) a second compound selected from the group consisting of;
      1) a secondary amine, wherein the secondary amine is chosen from the group consisting of;
         a) diethylamine, and
         b) diisopropylamine; and
      2) a tertiary amine, wherein the tertiary amine is chosen from the group consisting of;
         a) piperidine,
         b) N-methylpiperidine,
         c) N-methylpyrrolidine,
         d) triethylamine, and
         e) diisopropylethylamine.

8. The aqueous oligonucleotide cleaving reagent of claim 7, wherein the first compound is methylamine and the second compound is N-methylpyrrolidine.

9. The aqueous oligonucleotide cleaving reagent of claim 7, wherein the first compound is ammonium hydroxide and the second compound is triethylamine.

10. An aqueous oligonucleotide cleaving reagent consisting of about 20 wt. % methylamine and about 20 wt. % dimethylamine.

* * * * *